US011174461B2

(12) United States Patent
Slukvin et al.

(10) Patent No.: US 11,174,461 B2
(45) Date of Patent: Nov. 16, 2021

(54) COLONY FORMING MEDIUM AND USE THEREOF

(71) Applicant: CYNATA THERAPEUTICS LIMITED, Carlton (AU)

(72) Inventors: Igor Slukvin, Verona, WI (US); Gene Uenishi, San Francisco, CA (US); Derek Hei, Madison, WI (US); Diana Drier, Madison, WI (US)

(73) Assignee: Cynata Therapeutics Limited, Carlton (AU)

( * ) Notice: Subject to any disclaimer, the term of this patent is extended or adjusted under 35 U.S.C. 154(b) by 204 days.

(21) Appl. No.: 16/084,464

(22) PCT Filed: Mar. 14, 2017

(86) PCT No.: PCT/AU2017/050228
§ 371 (c)(1),
(2) Date: Sep. 12, 2018

(87) PCT Pub. No.: WO2017/156580
PCT Pub. Date: Sep. 21, 2017

(65) Prior Publication Data
US 2019/0071637 A1 Mar. 7, 2019

(30) Foreign Application Priority Data

Mar. 16, 2016 (AU) ................. 2016900983
Oct. 5, 2016 (AU) ................. 2016904039
Feb. 2, 2017 (AU) ................. 2017900318

(51) Int. Cl.
*A61K 35/28* (2015.01)
*C12N 5/0775* (2010.01)
(Continued)

(52) U.S. Cl.
CPC ............ *C12N 5/0606* (2013.01); *A61K 35/28* (2013.01); *A61P 9/00* (2018.01); *A61P 19/02* (2018.01);
(Continued)

(58) Field of Classification Search
CPC .. C12N 5/0606; C12N 5/0663; C12N 5/0665; C12N 2501/115; C12N 2501/155;
(Continued)

(56) References Cited

U.S. PATENT DOCUMENTS 7,615,374 B2    11/2009  Vodyanyk et al.
2009/0081784 A1*  3/2009  Vodyanyk ............ C12N 5/0662
                                                                   435/372
(Continued)

FOREIGN PATENT DOCUMENTS

CN    101384702 A    3/2009
CN    104160018 A    11/2014
(Continued)

OTHER PUBLICATIONS

Yangulov et al., "Influence of various cryoprotective media on the viability of cryopreserved lymphoblastic cell lines H-9 i U-937," Cryobiology problems, 1991, vol. 3, pp. 46-49 (4 pages).
(Continued)

*Primary Examiner* — Marcia S Noble
*Assistant Examiner* — Lauren K Van Buren
(74) *Attorney, Agent, or Firm* — Melissa Hunter-Ensor; Leslie Serunian; Greenberg Traurig, LLP

(57) ABSTRACT

The invention relates to a method for producing a mesenchymal stem cell (MSC), the method comprising culturing a primitive mesoderm cell in a mesenchymal colony forming medium (M-CFM) comprising LiCl and FGF2, but excluding PDGF, under normoxic conditions for sufficient time for a mesenchymal colony to form, and culturing the mesen-
(Continued)

GLECDGKVNI CCKKQFFVSF KDIGWNDWII APSGYHANYC EGECPSHIAG TSGSSLSFHS
TVINHYRMRG HSPFANLKSC CVPTKLRPMS MLYYDDGQNI IKKDIQNMIV EECGCS (SEQ ID NO: 1)

chymal colony adherently to produce the MSC, wherein the MSC has superior T-cell immunosuppressive properties relative to an MSC not produced in said M-CFM. The invention also relates to an MSC produced by the method, a population of MSCs produced by the method, a therapeutic composition comprising the MSC produced by the method, an M-CFM and an M-CFM in concentrated form, and method and uses of the MSC or population in treating a disease.

17 Claims, 10 Drawing Sheets

Specification includes a Sequence Listing.

(51) Int. Cl.
  *C12N 5/07* (2010.01)
  *C12N 5/0735* (2010.01)
  *A61P 9/00* (2006.01)
  *A61P 37/06* (2006.01)
  *A61P 19/02* (2006.01)
  *A61K 35/00* (2006.01)

(52) U.S. Cl.
  CPC ............ *A61P 37/06* (2018.01); *C12N 5/0662* (2013.01); *C12N 5/0663* (2013.01); *C12N 5/0665* (2013.01); *C12N 5/0668* (2013.01); *A61K 35/00* (2013.01); *C12N 2500/02* (2013.01); *C12N 2500/05* (2013.01); *C12N 2501/115* (2013.01); *C12N 2501/135* (2013.01); *C12N 2501/155* (2013.01); *C12N 2501/16* (2013.01); *C12N 2501/22* (2013.01); *C12N 2501/727* (2013.01); *C12N 2501/999* (2013.01); *C12N 2506/45* (2013.01); *C12N 2533/52* (2013.01); *C12N 2533/54* (2013.01)

(58) Field of Classification Search
  CPC ........ C12N 2501/22; A61P 9/00; A61P 37/06; A61P 19/02; A61K 35/28
  See application file for complete search history.

(56) References Cited

U.S. PATENT DOCUMENTS

| | | | | |
|---|---|---|---|---|
| 2014/0273211 | A1* | 9/2014 | Slukvin | C12N 5/0695 435/372 |
| 2014/0328807 | A1* | 11/2014 | Aggarwal | C12N 5/0662 424/93.7 |
| 2015/0191699 | A1 | 7/2015 | Wang et al. | |

FOREIGN PATENT DOCUMENTS

| | | |
|---|---|---|
| CN | 104487568 A | 4/2015 |
| CN | 105209609 A | 12/2015 |
| WO | 2005093044 A1 | 10/2005 |
| WO | 2009135905 A2 | 11/2009 |
| WO | 2013134378 A1 | 9/2013 |
| WO | 2013151725 A1 | 10/2013 |
| WO | 2014165131 A1 | 10/2014 |
| WO | 2015088414 A1 | 6/2015 |

OTHER PUBLICATIONS

English translation of relevant portion of Yangulov et al., "Influence of various cryoprotective media on the viability of cryopreserved lymphoblastic cell lines H-9 i U-937," Cryobiology problems, 1991, vol. 3, pp. 46-49 (1 page).

Kozhukharova, "New lines of human embryonic stem cells C612 i C910," Cytology, 2009, vol. 51, No. 7, pp. 551-558; p. 551 (8 pages).

English translation of relevant portion of Kozhukharova, "New lines of human embryonic stem cells C612 i C910," Cytology, 2009, vol. 51, No. 7, pp. 551-558; p. 551 (1 page).

Menzorov, "Mouse and Human Embryonic Stem Cells," Vavilov Journal of Genetics and Breeding, 2013, vol. 17, No. 2, pp. 234-245 (12 pages).

English translation of relevant portion of Menzorov, "Mouse and Human Embryonic Stem Cells," Vavilov Journal of Genetics and Breeding, 2013, vol. 17, No. 2, pp. 234-245 (1 page).

Menzorov et al., "Why are collections of cell lines needed," Vavilov Journal of Genetics and Breeding, 2016, vol. 20, No. 6, pp. 945-948; p. 947 (4 pages).

English translation of relevant portion of Menzorov et al., "Why are collections of cell lines needed," Vavilov Journal of Genetics and Breeding, 2016, vol. 20, No. 6, pp. 945-948; p. 947 (1 page).

Novokhatskij et al., "The problem of cell contamination and new approaches to the control of transplanted lines," Virology Issue, 1977, vol. 4, pp. 396-408; pp. 396, 407, 408 (14 pages).

English translation of relevant portions of Novokhatskij et al., "The problem of cell contamination and new approaches to the control of transplanted lines," Virology Issue, 1977, vol. 4, pp. 396-408; pp. 396, 407, 408 (1 page).

Patel et al., "Therapeutic Potential of Mesenchymal Stem Cells in Regenerative Medicine," Stem Cells International, 2013, vol. 2013, Article ID 496218, pp. 1-15 (16 pages).

Vechkanov et al., "Fundamentals of Cell Engineering: A Tutorial," Rostov na Donu, 2012, 136 pages; pp. 15, 16 (2 pages).

English translation of relevant portion of Vechkanov et al., "Fundamentals of Cell Engineering: A Tutorial," Rostov na Donu, 2012, 136 pages; pp. 15, 16 (1 page).

Zhdanov et al., "The secret of the third kingdom," Knowledge, 1975, 176 pages, pp. 124, 125 (3 pages).

English translation of relevant portions of Zhdanov et al., "The secret of the third kingdom," Knowledge, 1975, 176 pages, pp. 124, 125 (1 page).

English translation of Office Action received in corresponding Russian Patent Application No. 2018133339, dated May 19, 2020 (6 pages).

English translation of Search Report received in corresponding Russian Patent Application No. 2018133339, dated May 19, 2020 (2 pages).

Extended European Search Report for corresponding European Patent Application No. 17765572.7, dated Sep. 19, 2019 (7 pages).

Lecourt, S., "Characterization of distinct mesenchymal-like cell popluations from human skeletal muscle in situ and in vitro," Experimental Cell Research, vol. 316, pp. 2513-2526 (2010).

Bloom, D.D. et al., "A Reproducible Immunopotency Assay to Measure Mesenchymal Stromal Cell Mediated T cell Suppression," Cytotherapy, vol. 17, No. 2, pp. 140-151 (Feb. 2015).

LV, F.J. et al., "Concise Review: The Surface Markers and Identity of Human Mesenchymal," Stem Cells, vol. 32, pp. 1408-1419 (2014).

Clark, E.A. et al., "Consise Review: MicroRNA Function in Multipotent Mesenchymal Stromal Cells," Stem Cells, vol. 32, pp. 1074-1082 (2014).

International Search Report for corresponding PCT Patent Application No. PCT/AU2017/050228, dated May 26, 2017 (4 pages).

First Office Action and Search Report dated Apr. 25, 2021 in corresponding Chinese Patent Application No. 201780017613.8 (8 pages).

English translation of the First Office Action and Search Report dated Apr. 25, 2021 in corresponding Chinese Patent Application No. 201780017613.8 (8 pages).

Third Office Action dated Mar. 29, 2021 in corresponding Russian Patent Application No. 2018133339/10(054698) (5 pages).

English translation of the Third Office Action dated Mar. 29, 2021 in corresponding Russian Patent Application No. 2018133339/10(054698) (5 pages).

* cited by examiner

```
GLECDGKVNI CCKKQFFVSF KDIGWNDWII APSGYHANYC EGECPSHIAG TSGSSLSFHS
TVINHYRMRG HSPFANLKSC CVPTKLRPMS MLYYDDGQNI IKKDIQNMIV EECGCS
```

Figure 1.   (SEQ ID NO: 1)

```
KKNKNCRRHS LYVDFSDVGW NDWIVAPPGY QAFYCHGDCP FPLADHLNST NHAIVQTLVN
SVNSSIPKAC CVPTELSAIS MLYLDEYDKV VLKNYQEMVV EGCGCR
```

Figure 2.   (SEQ ID NO: 2)

```
QLSYGYDEKS TGGISVPGPM GPSGPRGLPG PPGAPGPQGF QGPPGEPGEP GASGPMGPRG
PPGPPGKNGD DGEAGKPGRP GERGPPGPQG ARGLPGTAGL PGMKGHRGFS GLDGAKGDAG
PAGPKGEPGS PGENGAPGQM GPRGLPGERG RPGAPGPAGA RGNDGATGAA GPPGPTGPAG
PPGFPGAVGA KGEAGPQGPR GSEGPQGVRG EPGPPGPAGA AGPAGNPGAD GQPGAKGANG
APGIAGAPGF PGARGPSGPQ GPGGPPGPKG NSGEPGAPGS KGDTGAKGEP GPVGVQGPPG
PAGEEGKRGA RGEPGPTGLP GPPGERGGPG SRGFPGADGV AGPKGPAGER GSPGPAGPKG
SPGEAGRPGE AGLPGAKGLT GSPGSPGPDG KTGPPGPAGQ DGRPGPPGPP GARGQAGVMG
FPGPKGAAGE PGKAGERGVP GPPGAVGPAG KDGEAGAQGP PGPAGPAGER GEQGPAGSPG
FQGLPGPAGP PGEAGKPGEQ GVPGDLGAPG PSGARGERGF PGERGVQGPP GPAGPRGANG
APGNDGAKGD AGAPGAPGSQ GAPGLQGMPG ERGAAGLPGP KGDRGDAGPK GADGSPGKDG
VRGLTGPIGP PGPAGAPGDK GESGPSGPAG PTGARGAPGD RGEPGPPGPA GFAGPPGADG
QPGAKGEPGD AGAKGDAGPP GPAGPAGPPG PIGNVGAPGA KGARGSAGPP GATGFPGAAG
RVGPPGPSGN AGPPGPPGPA GKEGGKGPRG ETGPAGRPGE VGPPGPPGPA GEKGSPGADG
PAGAPGTPGP QGIAGQRGVV GLPGQRGERG FPGLPGPSGE PGKQGPSGAS GERGPPGPMG
PPGLAGPPGE SGREGAPGAE GSPGRDGSPG AKGDRGETGP AGPPGAPGAP GAPGPVGPAG
KSGDRGETGP AGPAGPVGPV GARGPAGPQG PRGDKGETGE QGDRGIKGHR GFSGLQGPPG
PPGSPGEQGP SGASGPAGPR GPPGSAGAPG KDGLNGLPGP IGPPGPRGRT GDAGPVGPPG
PPGPPGPPGP PSAGFDFSFL PQPPQEKAHD GGRYYRA
```

Figure 3.   (SEQ ID NO: 3)

```
GERGFPGIPG  TPGPPGLPGL  QGPVGPPGFT  GPPGPPGPPG  PPGEKGQMGL  SFQGPKGDKG
DQGVSGPPGV  PGQAQVQEKG  DFATKGEKGQ  KGEPGFQGMP  GVGEKGEPGK  PGPRGKPGKD
GDKGEKGSPG  FPGEPGYPGL  IGRQGPQGEK  GEAGPPGPPG  IVIGTGPLGE  KGERGYPGTP
GPRGEPGPKG  FPGLPGQPGP  PGLPVPGQAG  APGFPGERGE  KGDRGFPGTS  LPGPSGRDGL
PGPPGSPGPP  GQPGYTNGIV  ECQPGPPGDQ  GPPGIPGQPG  FIGEIGEKGQ  KGESCLICDI
DGYRGPPGPQ  GPPGEIGFPG  QPGAKGDRGL  PGRDGVAGVP  GPQGTPGLIG  QPGAKGEPGE
FYFDLRLKGD  KGDPGFPGQP  GMPGRAGSPG  RDGHPGLPGP  KGSPGSVGLK  GERGPPGGVG
FPGSRGDTGP  PGPPGYGPAG  PIGDKGQAGF  PGGPGSPGLP  GPKGEPGKIV  PLPGPPGAEG
LPGSPGFPGP  QGDRGFPGTP  GRPGLPGEKG  AVGQPGIGFP  GPPGPKGVDG  LPGDMGPPGT
PGRPGFNGLP  GNPGVQGQKG  EPGVGLPGLK  GLPGLPGIPG  TPGEKGSIGV  PGVPGEHGAI
GPPGLQGIRG  EPGPPGLPGS  VGSPGVPGIG  PPGARGPPGG  QGPPGLSGPP  GIKGEKGFPG
FPGLDMPGPK  GDKGAQGLPG  ITGQSGLPGL  PGQQGAPGIP  GFPGSKGEMG  VMGTPGQPGS
PGPVGAPGLP  GEKGDHGFPG  SSGPRGDPGL  KGDKGDVGLP  GKPGSMDKVD  MGSMKGQKGD
QGEKGQIGPI  GEKGSRGDPG  TPGVPGKDGQ  AGQPGQPGPK  GDPGISGTPG  APGLPGPKGS
VGGMGLPGTP  GEKGVPGIPG  PQGSPGLPGD  KGAKGEKGQA  GPPGIGIPGL  RGEKGDQGIA
GFPGSPGEKG  EKGSIGIPGM  PGSPGLKGSP  GSVGYPGSPG  LPGEKGDKGL  PGLDGIPGVK
GEAGLPGTPG  PTGPAGQKGE  PGSDGIPGSA  GEKGEPGLPG  RGFPGFPGAK  GDKGSKGEVG
FPGLAGSPGI  PGSKGEQGFM  GPPGPQGQPG  LPGSPGHATE  GPKGDRGPQG  QPGLPGLPGP
MGPPGLPGID  GVKGDKGNPG  WPGAPGVPGP  KGDPGFQGMP  GIGGSPGITG  SKGDMGPPGV
PGFQGPKGLP  GLQGIKGDQG  DQGVPGAKGL  PGPPGPPGPY  DIIKGEPGLP  GPEGPPGLKG
LQGLPGPKGQ  QGVTGLVGIP  GPPGIPGFDG  APGQKGEMGP  AGPTGPRGFP  GPPGPDGLPG
SMGPPGTPSV  DHGFLVTRHS  QTIDDPQCPS  GTKILYHGYS  LLYVQGNERA  HGQDLGTAGS
CLRKFSTMPF  LFCNINNVCN  FASRNDYSYW  LSTPEPMPMS  MAPITGENIR  PFISRCAVCE
APAMVMAVHS  QTIQIPPCPS  GWSSLWIGYS  FVMHTSAGAE  GSGQALASPG  SCLEEFRSAP
FIECHGRGTC  NYYANAYSFW  LATIERSEMF  KKPTPSTLKA  GELRTHVSRC  QVCMRRT

Figure 4.   (SEQ ID NO: 4)

MVGVGGGDVE  DVTPRPGGCQ  ISGRGARGCN  GIPGAAAWEA  ALPRRRPRRH  PSVNPRSRAA
GSPRTRGRRT  EERPSGSRLG  DRGRGRALPG  GRLGGRGRGR  APERVGGRGR  GRGTAAPRAA
PAARGSRPGP  AGTMAAGSIT  TLPALPEDGG  SGAFPPGHFK  DPKRLYCKNG  GFFLRIHPDG
RVDGVREKSD  PHIKLQLQAE  ERGVVSIKGV  CANRYLAMKE  DGRLLASKCV  TDECFFFERL
ESNNYNTYRS  RKYTSWYVAL  KRTGQYKLGS  KTGPGQKAIL  FLPMSAKS

Figure 5.   (SEQ ID NO: 5)
```

```
QAQQMVQPQS PVAVSQSKPG CYDNGKHYQI NQQWERTYLG NALVCTCYGG SRGFNCESKP
EAEETCFDKY TGNTYRVGDT YERPKDSMIW DCTCIGAGRG RISCTIANRC HEGGQSYKIG
DTWRRPHETG GYMLECVCLG NGKGEWTCKP IAEKCFDHAA GTSYVVGETW EKPYQGWMMV
DCTCLGEGSG RITCTSRNRC NDQDTRTSYR IGDTWSKKDN RGNLLQCICT GNGRGEWKCE
RHTSVQTTSS GSGPFTDVRA AVYQPQPHPQ PPPYGHCVTD SGVVYSVGMQ WLKTQGNKQM
LCTCLGNGVS CQETAVTQTY GGNSNGEPCV LPFTYNGRTF YSCTTEGRQD GHLWCSTTSN
YEQDQKYSFC TDHTVLVQTR GGNSNGALCH FPFLYNNHNY TDCTSEGRRD NMKWCGTTQN
YDADQKFGFC PMAAHEEICT TNEGVMYRIG DQWDKQHDMG HMMRCTCVGN GRGEWTCIAY
SQLRDQCIVD DITYNVNDTF HKRHEEGHML NCTCFGQGRG RWKCDPVDQC QDSETGTFYQ
IGDSWEKYVH GVRYQCYCYG RGIGEWHCQP LQTYPSSSGP VEVFITETPS QPNSHPIQWN
APQPSHISKY ILRWRPKNSV GRWKEATIPG HLNSYTIKGL KPGVVYEGQL ISIQQYGHQE
VTRFDFTTTS TSTPVTSNTV TGETTPFSPL VATSESVTEI TASSFVVSWV SASDTVSGFR
VEYELSEEGD EPQYLDLPST ATSVNIPDLL PGRKYIVNVY QISEDGEQSL ILSTSQTTAP
DAPPDPTVDQ VDDTSIVVRW SRPQAPITGY RIVYSPSVEG SSTELNLPET ANSVTLSDLQ
PGVQYNITIY AVEENQESTP VVIQQETTGT PRSDTVPSPR DLQFVEVTDV KVTIMWTPPE
SAVTGYRVDV IPVNLPGEHG QRLPISRNTF AEVTGLSPGV TYYFKVFAVS HGRESKPLTA
QQTTKLDAPT NLQFVNETDS TVLVRWTPPR AQITGYRLTV GLTRRGQPRQ YNVGPSVSKY
PLRNLQPASE YTVSLVAIKG NQESPKATGV FTTLQPGSSI PPYNTEVTET TIVITWTPAP
RIGFKLGVRP SQGGEAPREV TSDSGSIVVS GLTPGVEYVY TIQVLRDGQE RDAPIVNKVV
TPLSPPTNLH LEANPDTGVL TVSWERSTTP DITGYRITTT PTNGQQGNSL EEVVHADQSS
CTFDNLSPGL EYNVSVYTVK DDKESVPISD TIIPEVPQLT DLSFVDITDS SIGLRWTPLN
SSTIIGYRIT VVAAGEGIPI FEDFVDSSVG YYTVTGLEPG IDYDISVITL INGGESAPTT
LTQQTAVPPP TDLRFTNIGP DTMRVTWAPP PSIDLTNFLV RYSPVKNEED VAELSISPSD
NAVVLTNLLP GTEYVVSVSS VYEQHESTPL RGRQKTGLDS PTGIDFSDIT ANSFTVHWIA
PRATITGYRI RHHPEHFSGR PREDRVPHSR NSITLTNLTP GTEYVVSIVA LNGREESPLL
IGQQSTVSDV PRDLEVVAAT PTSLLISWDA PAVTVRYYRI TYGETGGNSP VQEFTVPGSK
STATISGLKP GVDYTITVYA VTGRGDSPAS SKPISINYRT EIDKPSQMQV TDVQDNSISV
KWLPSSSPVT GYRVTTTPKN GPGPTKTKTA GPDQTEMTIE GLQPTVEYVV SVYAQNPSGE
SQPLVQTAVT NIDRPKGLAF TDVDVDSIKI AWESPQGQVS RYRVTYSSPE DGIHELFPAP
DGEEDTAELQ GLRPGSEYTV SVVALHDDME SQPLIGTQST AIPAPTDLKF TQVTPTSLSA
QWTPPNVQLT GYRVRVTPKE KTGPMKEINL APDSSSVVVS GLMVATKYEV SVYALKDTLT
SRPAQGVVTT LENVSPPRRA RVTDATETTI TISWRTKTET ITGFQVDAVP ANGQTPIQRT
IKPDVRSYTI TGLQPGTDYK IYLYTLNDNA RSSPVVIDAS TAIDAPSNLR FLATTPNSLL
VSWQPPRARI TGYIIKYEKP GSPPREVVPR PRPGVTEATI TGLEPGTEYT IYVIALKNNQ
KSEPLIGRKK TDELPQLVTL PHPNLHGPEI LDVPSTVQKT PFVTHPGYDT GNGIQLPGTS
GQQPSVGQQM IFEEHGFRRT TPPTTATPIR HRPRPYPPNV GQEALSQTTI SWAPFQDTSE
YIISCHPVGT DEEPLQFRVP GTSTSATLTG LTRGATYNII VEALKDQQRH KVREEVVTVG
NSVNEGLNQP TDDSCFDPYT VSHYAVGDEW ERMSESGFKL LCQCLGFGSG HFRCDSSRWC
HDNGVNYKIG EKWDRQGENG QMMSCTCLGN GKGEFKCDPH EATCYDDGKT YHVGEQWQKE
YLGAICSCTC FGGQRGWRCD NCRRPGGEPS PEGTTGQSYN QYSQRYHQRT NTNVNCPIEC
FMPLDVQADR EDSRE
```

Figure 6. (SEQ ID NO: 6)

```
SLGSLTIAEP AMIAECKTRT EVFEISRRLI DRTNANFLVW PPCVEVQRCS GCCNNRNVQC
RPTQVQLRPV QVRKIEIVRK KPIFKKATVT LEDHLACKCE TVAAARPVT
```

Figure 7.  (SEQ ID NO: 7)

```
GVLKKVIRHK RQSGVNATLP EENQPVVFNH VYNIKLPVGS QCSVDLESAS GEKDLAPPSE
PSESFQEHTV DGENQIVFTH RINIPRRACG CAAAPDVKEL LSRLEELENL VSSLREQCTA
GAGCCLQPAT GRLDTRPFCS GRGNFSTEGC GCVCEPGWKG PNCSEPECPG NCHLRGRCID
GQCICDDGFT GEDCSQLACP SDCNDQGKCV NGVCICFEGY AGADCSREIC PVPCSEEHGT
CVDGLCVCHD GFAGDDCNKP LCLNNCYNRG RCVENECVCD EGFTGEDCSE LICPNDCFDR
GRCINGTCYC EEGFTGEDCG KPTCPHACHT QGRCEEGQCV CDEGFAGVDC SEKRCPADCH
NRGRCVDGRC ECDDGFTGAD CGELKCPNGC SGHGRCVNGQ CVCDEGYTGE DCSQLRCPND
CHSRGRCVEG KCVCEQGFKG YDCSDMSCPN DCHQHGRCVN GMCVCDDGYT GEDCRDRQCP
RDCSNRGLCV DGQCVCEDGF TGPDCAELSC PNDCHGQGRC VNGQCVCHEG FMGKDCKEQR
CPSDCHGQGR CVDGQCICHE GFTGLDCGQH SCPSDCNNLG QCVSGRCICN EGYSGEDCSE
VSPPKDLVVT EVTEETVNLA WDNEMRVTEY LVVYTPTHEG GLEMQFRVPG DQTSTIIQEL
EPGVEYFIRV FAILENKKSI PVSARVATYL PAPEGLKFKS IKETSVEVEW DPLDIAFETW
EIIFRNMNKE DEGEITKSLR RPETSYRQTG LAPGQEYEIS LHIVKNNTRG PGLKRVTTTR
LDAPSQIEVK DVTDTTALIT WFKPLAEIDG IELTYGIKDV PGDRTTIDLT EDENQYSIGN
LKPDTEYEVS LISRRGDMSS NPAKETFTTG LDAPRNLRRV SQTDNSITLE WRNGKAAIDS
YRIKYAPISG GDHAEVDVPK SQQATTKTTL TGLRPGTEYG IGVSAVKEDK ESNPATINAA
TELDTPKDLQ VSETAETSLT LLWKTPLAKF DRYRLNYSLP TGQWVGVQLP RNTTSYVLRG
LEPGQEYNVL LTAEKGRHKS KPARVKASTE QAPELENLTV TEVGWDGLRL NWTAADQAYE
HFIIQVQEAN KVEAARNLTV PGSLRAVDIP GLKAATPYTV SIYGVIQGYR TPVLSAEAST
GETPNLGEVV VAEVGWDALK LNWTAPEGAY EYFFIQVQEA DTVEAAQNLT VPGGLRSTDL
PGLKAATHYT ITIRGVTQDF STTPLSVEVL TEEVPDMGNL TVTEVSWDAL RLNWTTPDGT
YDQFTIQVQE ADQVEEAHNL TVPGSLRSME IPGLRAGTPY TVTLHGEVRG HSTRPLAVEV
VTEDLPQLGD LAVSEVGWDG LRLNWTAADN AYEHFVIQVQ EVNKVEAAQN LTLPGSLRAV
DIPGLEAATP YRVSIYGVIR GYRTPVLSAE ASTAKEPEIG NLNVSDITPE SFNLSWMATD
GIFETFTIEI IDSNRLLETV EYNISGAERT AHISGLPPST DFIVYLSGLA PSIRTKTISA
TATTEALPLL ENLTISDINP YGFTVSWMAS ENAFDSFLVT VVDSGKLLDP QEFTLSGTQR
KLELRGLITG IGYEVMVSGF TQGHQTKPLR AEIVTEAEPE VDNLLVSDAT PDGFRLSWTA
DEGVFDNFVL KIRDTKKQSE PLEITLLAPE RTRDITGLRE ATEYEIELYG ISKGRRSQTV
SAIATTAMGS PKEVIFSDIT ENSATVSWRA PTAQVESFRI TYVPITGGTP SMVTVDGTKT
QTRLVKLIPG VEYLVSIIAM KGFEESEPVS GSFTTALDGP SGLVTANITD SEALARWQPA
IATVDSYVIS YTGEKVPEIT RTVSGNTVEY ALTDLEPATE YTLRIFAEKG PQKSSTITAK
FTTDLDSPRD LTATEVQSET ALLTWRPPRA SVTGYLLVYE SVDGTVKEVI VGPDTTSYSL
ADLSPSTHYT AKIQALNGPL RSNMIQTIFT TIGLLYPFPK DCSQAMLNGD TTSGLYTIYL
NGDKAEALEV FCDMTSDGGG WIVFLRRKNG RENFYQNWKA YAAGFGDRRE EFWLGLDNLN
KITAQGQYEL RVDLRDHGET AFAVYDKFSV GDAKTRYKLK VEGYSGTAGD SMAYHNGRSF
STFDKDTDSA ITNCALSYKG AFWYRNCHRV NLMGRYGDNN HSQGVNWFHW KGHEHSIQFA
EMKLRPSNFR NLEGRRKRA
```

Figure 8.  (SEQ ID NO: 8)

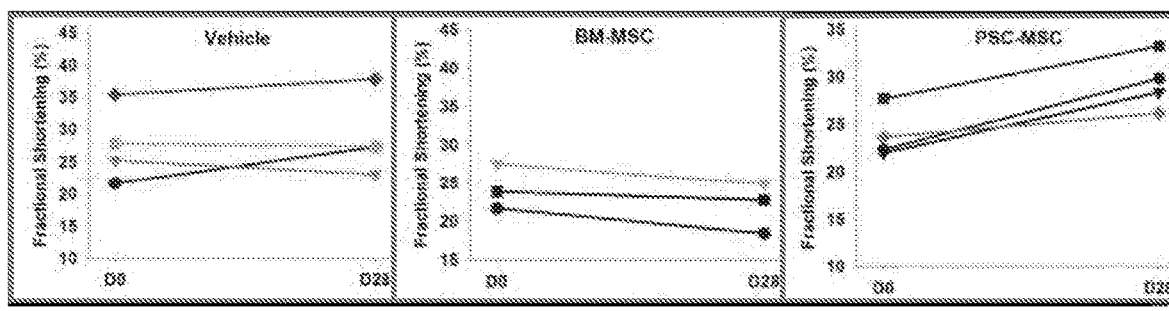
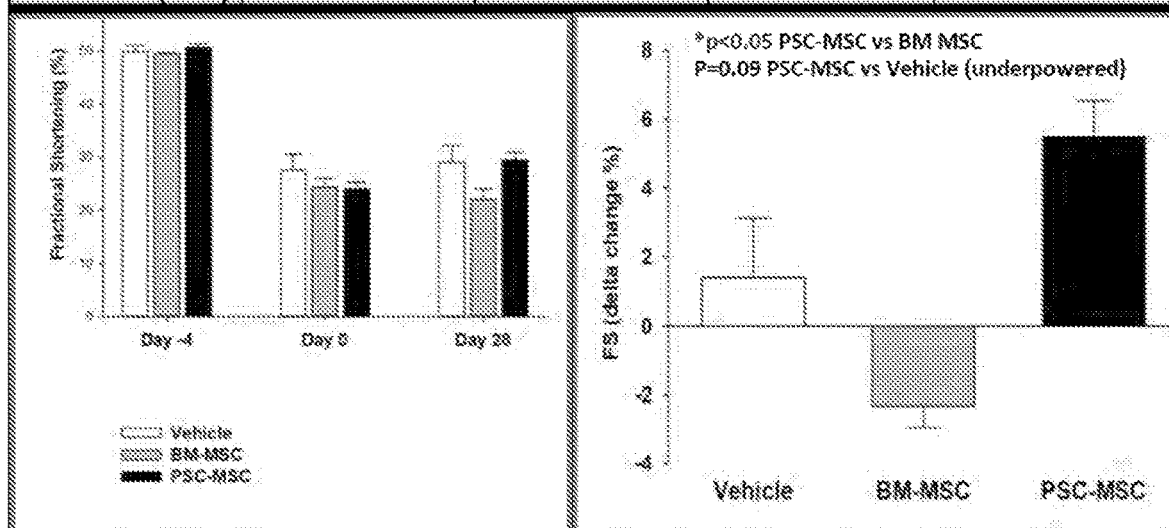
Figure 14.
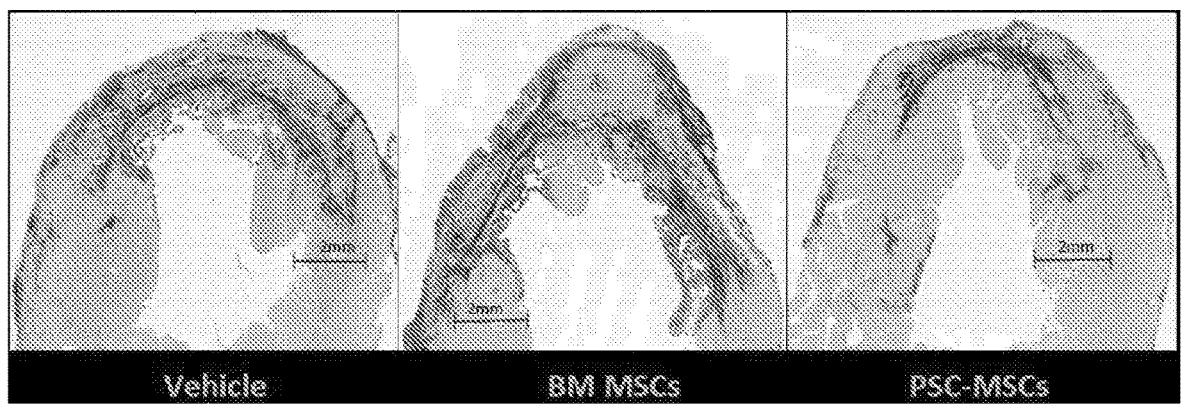
Figure 15.

SEQUENCE LISTING

```
<160> NUMBER OF SEQ ID NOS: 8

<210> SEQ ID NO 1
<211> LENGTH: 116
<212> TYPE: PRT
<213> ORGANISM: Homo sapiens

<400> SEQUENCE: 1

Gly Leu Glu Cys Asp Gly Lys Val Asn Ile Cys Cys Lys Lys Gln Phe
1               5                   10                  15

Phe Val Ser Phe Lys Asp Ile Gly Trp Asn Asp Trp Ile Ile Ala Pro
                20                  25                  30

Ser Gly Tyr His Ala Asn Tyr Cys Glu Gly Glu Cys Pro Ser His Ile
            35                  40                  45

Ala Gly Thr Ser Gly Ser Ser Leu Ser Phe His Ser Thr Val Ile Asn
        50                  55                  60

His Tyr Arg Met Arg Gly His Ser Pro Phe Ala Asn Leu Lys Ser Cys
65                  70                  75                  80

Cys Val Pro Thr Lys Leu Arg Pro Met Ser Met Leu Tyr Tyr Asp Asp
                85                  90                  95

Gly Gln Asn Ile Ile Lys Lys Asp Ile Gln Asn Met Ile Val Glu Glu
                100                 105                 110

Cys Gly Cys Ser
        115

<210> SEQ ID NO 2
<211> LENGTH: 106
<212> TYPE: PRT
<213> ORGANISM: Homo sapiens

<400> SEQUENCE: 2

Lys Lys Asn Lys Asn Cys Arg Arg His Ser Leu Tyr Val Asp Phe Ser
1               5                   10                  15

Asp Val Gly Trp Asn Asp Trp Ile Val Ala Pro Pro Gly Tyr Gln Ala
                20                  25                  30

Phe Tyr Cys His Gly Asp Cys Pro Phe Pro Leu Ala Asp His Leu Asn
```

```
                    35                  40                  45
Ser Thr Asn His Ala Ile Val Gln Thr Leu Val Asn Ser Val Asn Ser
 50                  55                  60

Ser Ile Pro Lys Ala Cys Cys Val Pro Thr Glu Leu Ser Ala Ile Ser
 65                  70                  75                  80

Met Leu Tyr Leu Asp Glu Tyr Asp Lys Val Leu Lys Asn Tyr Gln
                     85                  90                  95

Glu Met Val Val Glu Gly Cys Gly Cys Arg
                    100                 105

<210> SEQ ID NO 3
<211> LENGTH: 1057
<212> TYPE: PRT
<213> ORGANISM: Homo sapiens

<400> SEQUENCE: 3

Gln Leu Ser Tyr Gly Tyr Asp Glu Lys Ser Thr Gly Gly Ile Ser Val
 1                   5                  10                  15

Pro Gly Pro Met Gly Pro Ser Gly Pro Arg Gly Leu Pro Gly Pro Pro
                    20                  25                  30

Gly Ala Pro Gly Pro Gln Gly Phe Gln Gly Pro Pro Gly Glu Pro Gly
                    35                  40                  45

Glu Pro Gly Ala Ser Gly Pro Met Gly Pro Arg Gly Pro Pro Gly Pro
 50                  55                  60

Pro Gly Lys Asn Gly Asp Asp Gly Glu Ala Gly Lys Pro Gly Arg Pro
 65                  70                  75                  80

Gly Glu Arg Gly Pro Pro Gly Pro Gln Gly Ala Arg Gly Leu Pro Gly
                    85                  90                  95

Thr Ala Gly Leu Pro Gly Met Lys Gly His Arg Gly Phe Ser Gly Leu
                   100                 105                 110

Asp Gly Ala Lys Gly Asp Ala Gly Pro Ala Gly Pro Lys Gly Glu Pro
                   115                 120                 125

Gly Ser Pro Gly Glu Asn Gly Ala Pro Gly Gln Met Gly Pro Arg Gly
                   130                 135                 140

Leu Pro Gly Glu Arg Gly Arg Pro Gly Ala Pro Gly Pro Ala Gly Ala
145                 150                 155                 160

Arg Gly Asn Asp Gly Ala Thr Gly Ala Ala Gly Pro Pro Gly Pro Thr
                   165                 170                 175

Gly Pro Ala Gly Pro Pro Gly Phe Pro Gly Ala Val Gly Ala Lys Gly
                   180                 185                 190

Glu Ala Gly Pro Gln Gly Pro Arg Gly Ser Glu Gly Pro Gln Gly Val
                   195                 200                 205

Arg Gly Glu Pro Gly Pro Pro Gly Pro Ala Gly Ala Ala Gly Pro Ala
                   210                 215                 220

Gly Asn Pro Gly Ala Asp Gly Gln Pro Gly Ala Lys Gly Ala Asn Gly
225                 230                 235                 240

Ala Pro Gly Ile Ala Gly Ala Pro Gly Phe Pro Gly Ala Arg Gly Pro
                   245                 250                 255

Ser Gly Pro Gln Gly Pro Gly Gly Pro Pro Gly Pro Lys Gly Asn Ser
                   260                 265                 270

Gly Glu Pro Gly Ala Pro Gly Ser Lys Gly Asp Thr Gly Ala Lys Gly
                   275                 280                 285

Glu Pro Gly Pro Val Gly Val Gln Gly Pro Pro Gly Pro Ala Gly Glu
                   290                 295                 300
```

```
Glu Gly Lys Arg Gly Arg Gly Glu Pro Gly Pro Thr Gly Leu Pro
305                 310                 315                 320

Gly Pro Pro Gly Glu Arg Gly Gly Pro Gly Ser Arg Gly Phe Pro Gly
                325                 330                 335

Ala Asp Gly Val Ala Gly Pro Lys Gly Pro Ala Gly Glu Arg Gly Ser
            340                 345                 350

Pro Gly Pro Ala Gly Pro Lys Gly Ser Pro Gly Glu Ala Gly Arg Pro
        355                 360                 365

Gly Glu Ala Gly Leu Pro Gly Ala Lys Gly Leu Thr Gly Ser Pro Gly
370                 375                 380

Ser Pro Gly Pro Asp Gly Lys Thr Gly Pro Pro Gly Pro Ala Gly Gln
385                 390                 395                 400

Asp Gly Arg Pro Gly Pro Pro Gly Pro Ala Arg Gly Gln Ala
            405                 410                 415

Gly Val Met Gly Phe Pro Gly Pro Lys Gly Ala Ala Gly Glu Pro Gly
            420                 425                 430

Lys Ala Gly Glu Arg Gly Val Pro Gly Pro Pro Gly Ala Val Gly Pro
        435                 440                 445

Ala Gly Lys Asp Gly Glu Ala Gly Ala Gln Gly Pro Pro Gly Pro Ala
450                 455                 460

Gly Pro Ala Gly Glu Arg Gly Glu Gln Gly Pro Ala Gly Ser Pro Gly
465                 470                 475                 480

Phe Gln Gly Leu Pro Gly Pro Ala Gly Pro Pro Gly Glu Ala Gly Lys
            485                 490                 495

Pro Gly Glu Gln Gly Val Pro Gly Asp Leu Gly Ala Pro Gly Pro Ser
        500                 505                 510

Gly Ala Arg Gly Glu Arg Gly Phe Pro Gly Glu Arg Gly Val Gln Gly
            515                 520                 525

Pro Pro Gly Pro Ala Gly Pro Arg Gly Ala Asn Gly Ala Pro Gly Asn
530                 535                 540

Asp Gly Ala Lys Gly Asp Ala Gly Ala Pro Gly Ala Pro Gly Ser Gln
545                 550                 555                 560

Gly Ala Pro Gly Leu Gln Gly Met Pro Gly Glu Arg Gly Ala Ala Gly
            565                 570                 575

Leu Pro Gly Pro Lys Gly Asp Arg Gly Asp Ala Gly Pro Lys Gly Ala
        580                 585                 590

Asp Gly Ser Pro Gly Lys Asp Gly Val Arg Gly Leu Thr Gly Pro Ile
            595                 600                 605

Gly Pro Pro Gly Pro Ala Gly Ala Pro Gly Asp Lys Gly Glu Ser Gly
        610                 615                 620

Pro Ser Gly Pro Ala Gly Pro Thr Gly Ala Arg Gly Ala Pro Gly Asp
625                 630                 635                 640

Arg Gly Glu Pro Gly Pro Pro Gly Pro Ala Gly Phe Ala Gly Pro Pro
            645                 650                 655

Gly Ala Asp Gly Gln Pro Gly Ala Lys Gly Glu Pro Gly Asp Ala Gly
            660                 665                 670

Ala Lys Gly Asp Ala Gly Pro Pro Gly Pro Ala Gly Pro Ala Gly Pro
        675                 680                 685

Pro Gly Pro Ile Gly Asn Val Gly Ala Pro Gly Ala Lys Gly Ala Arg
            690                 695                 700

Gly Ser Ala Gly Pro Pro Gly Ala Thr Gly Phe Pro Gly Ala Ala Gly
705                 710                 715                 720

Arg Val Gly Pro Pro Gly Pro Ser Gly Asn Ala Gly Pro Pro Gly Pro
```

```
                    725                 730                 735
Pro Gly Pro Ala Gly Lys Glu Gly Lys Gly Pro Arg Gly Glu Thr
            740                 745                 750
Gly Pro Ala Gly Arg Pro Gly Glu Val Gly Pro Pro Gly Pro Gly
            755                 760                 765
Pro Ala Gly Glu Lys Gly Ser Pro Gly Ala Asp Gly Pro Ala Gly Ala
        770                 775                 780
Pro Gly Thr Pro Gly Pro Gln Gly Ile Ala Gly Gln Arg Gly Val Val
785                 790                 795                 800
Gly Leu Pro Gly Gln Arg Gly Glu Arg Gly Phe Pro Gly Leu Pro Gly
                805                 810                 815
Pro Ser Gly Glu Pro Gly Lys Gln Gly Pro Ser Gly Ala Ser Gly Glu
            820                 825                 830
Arg Gly Pro Pro Gly Pro Met Gly Pro Pro Gly Leu Ala Gly Pro Pro
            835                 840                 845
Gly Glu Ser Gly Arg Glu Gly Ala Pro Gly Ala Glu Gly Ser Pro Gly
            850                 855                 860
Arg Asp Gly Ser Pro Gly Ala Lys Gly Asp Arg Gly Glu Thr Gly Pro
865                 870                 875                 880
Ala Gly Pro Pro Gly Ala Pro Gly Ala Pro Gly Ala Pro Gly Pro Val
                885                 890                 895
Gly Pro Ala Gly Lys Ser Gly Asp Arg Gly Glu Thr Gly Pro Ala Gly
            900                 905                 910
Pro Ala Gly Pro Val Gly Pro Val Gly Ala Arg Gly Pro Ala Gly Pro
            915                 920                 925
Gln Gly Pro Arg Gly Asp Lys Gly Glu Thr Gly Glu Gln Gly Asp Arg
        930                 935                 940
Gly Ile Lys Gly His Arg Gly Phe Ser Gly Leu Gln Gly Pro Pro Gly
945                 950                 955                 960
Pro Pro Gly Ser Pro Gly Glu Gln Gly Pro Ser Gly Ala Ser Gly Pro
                965                 970                 975
Ala Gly Pro Arg Gly Pro Pro Gly Ser Ala Gly Ala Pro Gly Lys Asp
            980                 985                 990
Gly Leu Asn Gly Leu Pro Gly Pro Ile Gly Pro Pro Gly Pro Arg Gly
            995                 1000                1005
Arg Thr Gly Asp Ala Gly Pro Val Gly Pro Pro Gly Pro Pro Gly
        1010                1015                1020
Pro Pro Gly Pro Pro Gly Pro Pro Ser Ala Gly Phe Asp Phe Ser
        1025                1030                1035
Phe Leu Pro Gln Pro Pro Gln Glu Lys Ala His Asp Gly Gly Arg
        1040                1045                1050

Tyr Tyr Arg Ala
        1055

<210> SEQ ID NO 4
<211> LENGTH: 1497
<212> TYPE: PRT
<213> ORGANISM: Homo sapiens

<400> SEQUENCE: 4

Gly Glu Arg Gly Phe Pro Gly Ile Pro Gly Thr Pro Gly Pro Pro Gly
1               5                   10                  15
Leu Pro Gly Leu Gln Gly Pro Val Gly Pro Pro Gly Phe Thr Gly Pro
                20                  25                  30
```

-continued

```
Pro Gly Pro Gly Pro Gly Pro Gly Pro Gly Glu Lys Gly Gln Met
         35                  40                  45
Gly Leu Ser Phe Gln Gly Pro Lys Gly Asp Lys Gly Asp Gln Gly Val
 50                  55                  60
Ser Gly Pro Pro Gly Val Pro Gly Gln Ala Gln Val Gln Glu Lys Gly
 65                  70                  75                  80
Asp Phe Ala Thr Lys Gly Glu Lys Gly Gln Lys Gly Glu Pro Gly Phe
                 85                  90                  95
Gln Gly Met Pro Gly Val Gly Glu Lys Gly Glu Pro Gly Lys Pro Gly
             100                 105                 110
Pro Arg Gly Lys Pro Gly Lys Asp Gly Asp Lys Gly Glu Lys Gly Ser
         115                 120                 125
Pro Gly Phe Pro Gly Glu Pro Gly Tyr Pro Gly Leu Ile Gly Arg Gln
         130                 135                 140
Gly Pro Gln Gly Glu Lys Gly Glu Ala Gly Pro Pro Gly Pro Pro Gly
145                 150                 155                 160
Ile Val Ile Gly Thr Gly Pro Leu Gly Glu Lys Gly Glu Arg Gly Tyr
                 165                 170                 175
Pro Gly Thr Pro Gly Pro Arg Gly Glu Pro Gly Pro Lys Gly Phe Pro
             180                 185                 190
Gly Leu Pro Gly Gln Pro Gly Pro Pro Gly Leu Pro Val Pro Gly Gln
         195                 200                 205
Ala Gly Ala Pro Gly Phe Pro Gly Glu Arg Gly Glu Lys Gly Asp Arg
         210                 215                 220
Gly Phe Pro Gly Thr Ser Leu Pro Gly Pro Ser Gly Arg Asp Gly Leu
225                 230                 235                 240
Pro Gly Pro Pro Gly Ser Pro Gly Pro Pro Gly Gln Pro Gly Tyr Thr
                 245                 250                 255
Asn Gly Ile Val Glu Cys Gln Pro Gly Pro Pro Gly Asp Gln Gly Pro
             260                 265                 270
Pro Gly Ile Pro Gly Gln Pro Gly Phe Ile Gly Glu Ile Gly Glu Lys
         275                 280                 285
Gly Gln Lys Gly Glu Ser Cys Leu Ile Cys Asp Ile Asp Gly Tyr Arg
         290                 295                 300
Gly Pro Pro Gly Pro Gln Gly Pro Pro Gly Glu Ile Gly Phe Pro Gly
305                 310                 315                 320
Gln Pro Gly Ala Lys Gly Asp Arg Gly Leu Pro Gly Arg Asp Gly Val
                 325                 330                 335
Ala Gly Val Pro Gly Pro Gln Gly Thr Pro Gly Leu Ile Gly Gln Pro
             340                 345                 350
Gly Ala Lys Gly Glu Pro Gly Glu Phe Tyr Phe Asp Leu Arg Leu Lys
         355                 360                 365
Gly Asp Lys Gly Asp Pro Gly Phe Pro Gly Gln Pro Gly Met Pro Gly
         370                 375                 380
Arg Ala Gly Ser Pro Gly Arg Asp Gly His Pro Gly Leu Pro Gly Pro
385                 390                 395                 400
Lys Gly Ser Pro Gly Ser Val Gly Leu Lys Gly Glu Arg Gly Pro Pro
                 405                 410                 415
Gly Gly Val Gly Phe Pro Gly Ser Arg Gly Asp Thr Gly Pro Pro Gly
             420                 425                 430
Pro Pro Gly Tyr Gly Pro Ala Gly Pro Ile Gly Asp Lys Gly Gln Ala
         435                 440                 445
Gly Phe Pro Gly Gly Pro Gly Ser Pro Gly Leu Pro Gly Pro Lys Gly
```

```
            450                 455                 460
Glu Pro Gly Lys Ile Val Pro Leu Pro Gly Pro Pro Gly Ala Glu Gly
465                 470                 475                 480

Leu Pro Gly Ser Pro Gly Phe Pro Gly Pro Gln Gly Asp Arg Gly Phe
                485                 490                 495

Pro Gly Thr Pro Gly Arg Pro Gly Leu Pro Gly Glu Lys Gly Ala Val
            500                 505                 510

Gly Gln Pro Gly Ile Gly Phe Pro Gly Pro Pro Gly Pro Lys Gly Val
            515                 520                 525

Asp Gly Leu Pro Gly Asp Met Gly Pro Pro Gly Thr Pro Gly Arg Pro
            530                 535                 540

Gly Phe Asn Gly Leu Pro Gly Asn Pro Gly Val Gln Gly Gln Lys Gly
545                 550                 555                 560

Glu Pro Gly Val Gly Leu Pro Gly Leu Lys Gly Leu Pro Gly Leu Pro
                565                 570                 575

Gly Ile Pro Gly Thr Pro Gly Glu Lys Gly Ser Ile Gly Val Pro Gly
            580                 585                 590

Val Pro Gly Glu His Gly Ala Ile Gly Pro Pro Gly Leu Gln Gly Ile
            595                 600                 605

Arg Gly Glu Pro Gly Pro Pro Gly Leu Pro Gly Ser Val Gly Ser Pro
610                 615                 620

Gly Val Pro Gly Ile Gly Pro Pro Gly Ala Arg Gly Pro Pro Gly Gly
625                 630                 635                 640

Gln Gly Pro Pro Gly Leu Ser Gly Pro Pro Gly Ile Lys Gly Glu Lys
                645                 650                 655

Gly Phe Pro Gly Phe Pro Gly Leu Asp Met Pro Gly Pro Lys Gly Asp
                660                 665                 670

Lys Gly Ala Gln Gly Leu Pro Gly Ile Thr Gly Gln Ser Gly Leu Pro
            675                 680                 685

Gly Leu Pro Gly Gln Gln Gly Ala Pro Gly Ile Pro Gly Phe Pro Gly
            690                 695                 700

Ser Lys Gly Glu Met Gly Val Met Gly Thr Pro Gly Gln Pro Gly Ser
705                 710                 715                 720

Pro Gly Pro Val Gly Ala Pro Gly Leu Pro Gly Glu Lys Gly Asp His
                725                 730                 735

Gly Phe Pro Gly Ser Ser Gly Pro Arg Gly Asp Pro Gly Leu Lys Gly
                740                 745                 750

Asp Lys Gly Asp Val Gly Leu Pro Gly Lys Pro Gly Ser Met Asp Lys
            755                 760                 765

Val Asp Met Gly Ser Met Lys Gly Gln Lys Gly Asp Gln Gly Glu Lys
            770                 775                 780

Gly Gln Ile Gly Pro Ile Gly Glu Lys Gly Ser Arg Gly Asp Pro Gly
785                 790                 795                 800

Thr Pro Gly Val Pro Gly Lys Asp Gly Gln Ala Gly Gln Pro Gly Gln
                805                 810                 815

Pro Gly Pro Lys Gly Asp Pro Gly Ile Ser Gly Thr Pro Gly Ala Pro
            820                 825                 830

Gly Leu Pro Gly Pro Lys Gly Ser Val Gly Gly Met Gly Leu Pro Gly
            835                 840                 845

Thr Pro Gly Glu Lys Gly Val Pro Gly Ile Pro Gly Pro Gln Gly Ser
            850                 855                 860

Pro Gly Leu Pro Gly Asp Lys Gly Ala Lys Gly Glu Lys Gly Gln Ala
865                 870                 875                 880
```

```
Gly Pro Pro Gly Ile Gly Ile Pro Gly Leu Arg Gly Glu Lys Gly Asp
            885                 890                 895

Gln Gly Ile Ala Gly Phe Pro Gly Ser Pro Gly Lys Gly Glu Lys
        900                 905                 910

Gly Ser Ile Gly Ile Pro Gly Met Pro Gly Ser Pro Gly Leu Lys Gly
        915                 920                 925

Ser Pro Gly Ser Val Gly Tyr Pro Gly Ser Pro Gly Leu Pro Gly Glu
        930                 935                 940

Lys Gly Asp Lys Gly Leu Pro Gly Leu Asp Gly Ile Pro Gly Val Lys
945                 950                 955                 960

Gly Glu Ala Gly Leu Pro Gly Thr Pro Gly Pro Thr Gly Pro Ala Gly
            965                 970                 975

Gln Lys Gly Glu Pro Gly Ser Asp Gly Ile Pro Gly Ser Ala Gly Glu
        980                 985                 990

Lys Gly Glu Pro Gly Leu Pro Gly Arg Gly Phe Pro Gly Phe Pro Gly
        995                 1000                1005

Ala Lys Gly Asp Lys Gly Ser Lys Gly Glu Val Gly Phe Pro Gly
    1010                1015                1020

Leu Ala Gly Ser Pro Gly Ile Pro Gly Ser Lys Gly Glu Gln Gly
    1025                1030                1035

Phe Met Gly Pro Pro Gly Pro Gln Gly Gln Pro Gly Leu Pro Gly
    1040                1045                1050

Ser Pro Gly His Ala Thr Glu Gly Pro Lys Gly Asp Arg Gly Pro
    1055                1060                1065

Gln Gly Gln Pro Gly Leu Pro Gly Leu Pro Gly Pro Met Gly Pro
    1070                1075                1080

Pro Gly Leu Pro Gly Ile Asp Gly Val Lys Gly Asp Lys Gly Asn
    1085                1090                1095

Pro Gly Trp Pro Gly Ala Pro Gly Val Pro Gly Pro Lys Gly Asp
    1100                1105                1110

Pro Gly Phe Gln Gly Met Pro Gly Ile Gly Gly Ser Pro Gly Ile
    1115                1120                1125

Thr Gly Ser Lys Gly Asp Met Gly Pro Pro Gly Val Pro Gly Phe
    1130                1135                1140

Gln Gly Pro Lys Gly Leu Pro Gly Leu Gln Gly Ile Lys Gly Asp
    1145                1150                1155

Gln Gly Asp Gln Gly Val Pro Gly Ala Lys Gly Leu Pro Gly Pro
    1160                1165                1170

Pro Gly Pro Pro Gly Pro Tyr Asp Ile Ile Lys Gly Glu Pro Gly
    1175                1180                1185

Leu Pro Gly Pro Glu Gly Pro Pro Gly Leu Lys Gly Leu Gln Gly
    1190                1195                1200

Leu Pro Gly Pro Lys Gly Gln Gln Gly Val Thr Gly Leu Val Gly
    1205                1210                1215

Ile Pro Gly Pro Pro Gly Ile Pro Gly Phe Asp Gly Ala Pro Gly
    1220                1225                1230

Gln Lys Gly Glu Met Gly Pro Ala Gly Pro Thr Gly Pro Arg Gly
    1235                1240                1245

Phe Pro Gly Pro Pro Gly Pro Asp Gly Leu Pro Gly Ser Met Gly
    1250                1255                1260

Pro Pro Gly Thr Pro Ser Val Asp His Gly Phe Leu Val Thr Arg
    1265                1270                1275
```

```
His Ser Gln Thr Ile Asp Asp Pro Gln Cys Pro Ser Gly Thr Lys
    1280                1285                1290

Ile Leu Tyr His Gly Tyr Ser Leu Leu Tyr Val Gln Gly Asn Glu
    1295                1300                1305

Arg Ala His Gly Gln Asp Leu Gly Thr Ala Gly Ser Cys Leu Arg
    1310                1315                1320

Lys Phe Ser Thr Met Pro Phe Leu Phe Cys Asn Ile Asn Asn Val
    1325                1330                1335

Cys Asn Phe Ala Ser Arg Asn Asp Tyr Ser Tyr Trp Leu Ser Thr
    1340                1345                1350

Pro Glu Pro Met Pro Met Ser Met Ala Pro Ile Thr Gly Glu Asn
    1355                1360                1365

Ile Arg Pro Phe Ile Ser Arg Cys Ala Val Cys Glu Ala Pro Ala
    1370                1375                1380

Met Val Met Ala Val His Ser Gln Thr Ile Gln Ile Pro Pro Cys
    1385                1390                1395

Pro Ser Gly Trp Ser Ser Leu Trp Ile Gly Tyr Ser Phe Val Met
    1400                1405                1410

His Thr Ser Ala Gly Ala Glu Gly Ser Gly Gln Ala Leu Ala Ser
    1415                1420                1425

Pro Gly Ser Cys Leu Glu Glu Phe Arg Ser Ala Pro Phe Ile Glu
    1430                1435                1440

Cys His Gly Arg Gly Thr Cys Asn Tyr Tyr Ala Asn Ala Tyr Ser
    1445                1450                1455

Phe Trp Leu Ala Thr Ile Glu Arg Ser Glu Met Phe Lys Lys Pro
    1460                1465                1470

Thr Pro Ser Thr Leu Lys Ala Gly Glu Leu Arg Thr His Val Ser
    1475                1480                1485

Arg Cys Gln Val Cys Met Arg Arg Thr
    1490                1495

<210> SEQ ID NO 5
<211> LENGTH: 288
<212> TYPE: PRT
<213> ORGANISM: Homo sapiens

<400> SEQUENCE: 5

Met Val Gly Val Gly Gly Gly Asp Val Glu Asp Val Thr Pro Arg Pro
1               5                   10                  15

Gly Gly Cys Gln Ile Ser Gly Arg Gly Ala Arg Gly Cys Asn Gly Ile
            20                  25                  30

Pro Gly Ala Ala Ala Trp Glu Ala Ala Leu Pro Arg Arg Pro Arg
        35                  40                  45

Arg His Pro Ser Val Asn Pro Arg Ser Arg Ala Ala Gly Ser Pro Arg
    50                  55                  60

Thr Arg Gly Arg Arg Thr Glu Glu Arg Pro Ser Gly Ser Arg Leu Gly
65                  70                  75                  80

Asp Arg Gly Arg Gly Arg Ala Leu Pro Gly Gly Arg Leu Gly Gly Arg
                85                  90                  95

Gly Arg Gly Arg Ala Pro Glu Arg Val Gly Gly Arg Gly Arg Gly Arg
            100                 105                 110

Gly Thr Ala Ala Pro Arg Ala Ala Pro Ala Ala Arg Gly Ser Arg Pro
        115                 120                 125

Gly Pro Ala Gly Thr Met Ala Ala Gly Ser Ile Thr Thr Leu Pro Ala
    130                 135                 140
```

-continued

```
Leu Pro Glu Asp Gly Gly Ser Gly Ala Phe Pro Pro Gly His Phe Lys
145                 150                 155                 160

Asp Pro Lys Arg Leu Tyr Cys Lys Asn Gly Phe Phe Leu Arg Ile
                165                 170                 175

His Pro Asp Gly Arg Val Asp Gly Val Arg Glu Lys Ser Asp Pro His
            180                 185                 190

Ile Lys Leu Gln Leu Gln Ala Glu Glu Arg Gly Val Val Ser Ile Lys
        195                 200                 205

Gly Val Cys Ala Asn Arg Tyr Leu Ala Met Lys Glu Asp Gly Arg Leu
    210                 215                 220

Leu Ala Ser Lys Cys Val Thr Asp Glu Cys Phe Phe Phe Glu Arg Leu
225                 230                 235                 240

Glu Ser Asn Asn Tyr Asn Thr Tyr Arg Ser Arg Lys Tyr Thr Ser Trp
                245                 250                 255

Tyr Val Ala Leu Lys Arg Thr Gly Gln Tyr Lys Leu Gly Ser Lys Thr
            260                 265                 270

Gly Pro Gly Gln Lys Ala Ile Leu Phe Leu Pro Met Ser Ala Lys Ser
        275                 280                 285

<210> SEQ ID NO 6
<211> LENGTH: 2415
<212> TYPE: PRT
<213> ORGANISM: Homo sapiens

<400> SEQUENCE: 6

Gln Ala Gln Gln Met Val Gln Pro Gln Ser Pro Val Ala Val Ser Gln
1               5                   10                  15

Ser Lys Pro Gly Cys Tyr Asp Asn Gly Lys His Tyr Gln Ile Asn Gln
                20                  25                  30

Gln Trp Glu Arg Thr Tyr Leu Gly Asn Ala Leu Val Cys Thr Cys Tyr
            35                  40                  45

Gly Gly Ser Arg Gly Phe Asn Cys Glu Ser Lys Pro Glu Ala Glu Glu
        50                  55                  60

Thr Cys Phe Asp Lys Tyr Thr Gly Asn Thr Tyr Arg Val Gly Asp Thr
65                  70                  75                  80

Tyr Glu Arg Pro Lys Asp Ser Met Ile Trp Asp Cys Thr Cys Ile Gly
                85                  90                  95

Ala Gly Arg Gly Arg Ile Ser Cys Thr Ile Ala Asn Arg Cys His Glu
            100                 105                 110

Gly Gly Gln Ser Tyr Lys Ile Gly Asp Thr Trp Arg Arg Pro His Glu
        115                 120                 125

Thr Gly Gly Tyr Met Leu Glu Cys Val Cys Leu Gly Asn Gly Lys Gly
    130                 135                 140

Glu Trp Thr Cys Lys Pro Ile Ala Glu Lys Cys Phe Asp His Ala Ala
145                 150                 155                 160

Gly Thr Ser Tyr Val Val Gly Glu Thr Trp Lys Pro Tyr Gln Gly
                165                 170                 175

Trp Met Met Val Asp Cys Thr Cys Leu Gly Glu Gly Ser Gly Arg Ile
            180                 185                 190

Thr Cys Thr Ser Arg Asn Arg Cys Asn Asp Gln Asp Thr Arg Thr Ser
        195                 200                 205

Tyr Arg Ile Gly Asp Thr Trp Ser Lys Lys Asp Asn Arg Gly Asn Leu
    210                 215                 220

Leu Gln Cys Ile Cys Thr Gly Asn Gly Arg Gly Glu Trp Lys Cys Glu
```

```
                225                 230                 235                 240
Arg His Thr Ser Val Gln Thr Ser Ser Gly Ser Gly Pro Phe Thr
                        245                 250                 255
Asp Val Arg Ala Ala Val Tyr Gln Pro Gln Pro His Pro Gln Pro Pro
                260                 265                 270
Pro Tyr Gly His Cys Val Thr Asp Ser Gly Val Val Tyr Ser Val Gly
                275                 280                 285
Met Gln Trp Leu Lys Thr Gln Gly Asn Lys Gln Met Leu Cys Thr Cys
        290                 295                 300
Leu Gly Asn Gly Val Ser Cys Gln Glu Thr Ala Val Thr Gln Thr Tyr
305                 310                 315                 320
Gly Gly Asn Ser Asn Gly Glu Pro Cys Val Leu Pro Phe Thr Tyr Asn
                        325                 330                 335
Gly Arg Thr Phe Tyr Ser Cys Thr Thr Glu Gly Arg Gln Asp Gly His
                340                 345                 350
Leu Trp Cys Ser Thr Thr Ser Asn Tyr Glu Gln Asp Gln Lys Tyr Ser
        355                 360                 365
Phe Cys Thr Asp His Thr Val Leu Val Gln Thr Arg Gly Gly Asn Ser
370                 375                 380
Asn Gly Ala Leu Cys His Phe Pro Phe Leu Tyr Asn Asn His Asn Tyr
385                 390                 395                 400
Thr Asp Cys Thr Ser Glu Gly Arg Arg Asp Asn Met Lys Trp Cys Gly
                        405                 410                 415
Thr Thr Gln Asn Tyr Asp Ala Asp Gln Lys Phe Gly Phe Cys Pro Met
                420                 425                 430
Ala Ala His Glu Glu Ile Cys Thr Thr Asn Glu Gly Val Met Tyr Arg
                435                 440                 445
Ile Gly Asp Gln Trp Asp Lys Gln His Asp Met Gly His Met Met Arg
        450                 455                 460
Cys Thr Cys Val Gly Asn Gly Arg Gly Glu Trp Thr Cys Ile Ala Tyr
465                 470                 475                 480
Ser Gln Leu Arg Asp Gln Cys Ile Val Asp Asp Ile Thr Tyr Asn Val
                        485                 490                 495
Asn Asp Thr Phe His Lys Arg His Glu Glu Gly His Met Leu Asn Cys
                500                 505                 510
Thr Cys Phe Gly Gln Gly Arg Gly Arg Trp Lys Cys Asp Pro Val Asp
                515                 520                 525
Gln Cys Gln Asp Ser Glu Thr Gly Thr Phe Tyr Gln Ile Gly Asp Ser
        530                 535                 540
Trp Glu Lys Tyr Val His Gly Val Arg Tyr Gln Cys Tyr Cys Tyr Gly
545                 550                 555                 560
Arg Gly Ile Gly Glu Trp His Cys Gln Pro Leu Gln Thr Tyr Pro Ser
                        565                 570                 575
Ser Ser Gly Pro Val Glu Val Phe Ile Thr Glu Thr Pro Ser Gln Pro
                580                 585                 590
Asn Ser His Pro Ile Gln Trp Asn Ala Pro Gln Pro Ser His Ile Ser
                595                 600                 605
Lys Tyr Ile Leu Arg Trp Arg Pro Lys Asn Ser Val Gly Arg Trp Lys
        610                 615                 620
Glu Ala Thr Ile Pro Gly His Leu Asn Ser Tyr Thr Ile Lys Gly Leu
625                 630                 635                 640
Lys Pro Gly Val Val Tyr Glu Gly Gln Leu Ile Ser Ile Gln Gln Tyr
                        645                 650                 655
```

```
Gly His Gln Glu Val Thr Arg Phe Asp Phe Thr Thr Ser Thr Ser
            660                 665                 670

Thr Pro Val Thr Ser Asn Thr Val Thr Gly Glu Thr Thr Pro Phe Ser
        675                 680                 685

Pro Leu Val Ala Thr Ser Glu Ser Val Thr Glu Ile Thr Ala Ser Ser
690                 695                 700

Phe Val Val Ser Trp Val Ser Ala Ser Asp Thr Val Ser Gly Phe Arg
705                 710                 715                 720

Val Glu Tyr Glu Leu Ser Glu Gly Asp Glu Pro Gln Tyr Leu Asp
            725                 730                 735

Leu Pro Ser Thr Ala Thr Ser Val Asn Ile Pro Asp Leu Leu Pro Gly
            740                 745                 750

Arg Lys Tyr Ile Val Asn Val Tyr Gln Ile Ser Glu Asp Gly Glu Gln
            755                 760                 765

Ser Leu Ile Leu Ser Thr Ser Gln Thr Thr Ala Pro Asp Ala Pro Pro
            770                 775                 780

Asp Pro Thr Val Asp Gln Val Asp Asp Thr Ser Ile Val Val Arg Trp
785                 790                 795                 800

Ser Arg Pro Gln Ala Pro Ile Thr Gly Tyr Arg Ile Val Tyr Ser Pro
            805                 810                 815

Ser Val Glu Gly Ser Ser Thr Glu Leu Asn Leu Pro Glu Thr Ala Asn
            820                 825                 830

Ser Val Thr Leu Ser Asp Leu Gln Pro Gly Val Gln Tyr Asn Ile Thr
            835                 840                 845

Ile Tyr Ala Val Glu Glu Asn Gln Glu Ser Thr Pro Val Val Ile Gln
850                 855                 860

Gln Glu Thr Thr Gly Thr Pro Arg Ser Asp Thr Val Pro Ser Pro Arg
865                 870                 875                 880

Asp Leu Gln Phe Val Glu Val Thr Asp Val Lys Val Thr Ile Met Trp
            885                 890                 895

Thr Pro Pro Glu Ser Ala Val Thr Gly Tyr Arg Val Asp Val Ile Pro
            900                 905                 910

Val Asn Leu Pro Gly Glu His Gly Gln Arg Leu Pro Ile Ser Arg Asn
            915                 920                 925

Thr Phe Ala Glu Val Thr Gly Leu Ser Pro Gly Val Thr Tyr Tyr Phe
            930                 935                 940

Lys Val Phe Ala Val Ser His Gly Arg Glu Ser Lys Pro Leu Thr Ala
945                 950                 955                 960

Gln Gln Thr Thr Lys Leu Asp Ala Pro Thr Asn Leu Gln Phe Val Asn
                965                 970                 975

Glu Thr Asp Ser Thr Val Leu Val Arg Trp Thr Pro Arg Ala Gln
            980                 985                 990

Ile Thr Gly Tyr Arg Leu Thr Val  Gly Leu Thr Arg Arg  Gly Gln Pro
            995                 1000                1005

Arg Gln  Tyr Asn Val Gly Pro  Ser Val Ser Lys Tyr  Pro Leu Arg
    1010                1015                1020

Asn Leu  Gln Pro Ala Ser Glu  Tyr Thr Val Ser Leu  Val Ala Ile
    1025                1030                1035

Lys Gly  Asn Gln Glu Ser Pro  Lys Ala Thr Gly Val  Phe Thr Thr
    1040                1045                1050

Leu Gln  Pro Gly Ser Ser Ile  Pro Pro Tyr Asn Thr  Glu Val Thr
    1055                1060                1065
```

-continued

| | | | | | | | | | | |
|---|---|---|---|---|---|---|---|---|---|---|
| Glu | Thr | Thr | Ile | Val | Ile | Thr | Trp | Thr | Pro | Ala | Pro | Arg | Ile | Gly |
| 1070 | | | | | 1075 | | | | | 1080 | | | | |

Phe Lys Leu Gly Val Arg Pro Ser Gln Gly Gly Glu Ala Pro Arg
1085                     1090                    1095

Glu Val Thr Ser Asp Ser Gly Ser Ile Val Val Ser Gly Leu Thr
1100                    1105                    1110

Pro Gly Val Glu Tyr Val Tyr Thr Ile Gln Val Leu Arg Asp Gly
1115                    1120                    1125

Gln Glu Arg Asp Ala Pro Ile Val Asn Lys Val Val Thr Pro Leu
1130                    1135                    1140

Ser Pro Pro Thr Asn Leu His Leu Glu Ala Asn Pro Asp Thr Gly
1145                    1150                    1155

Val Leu Thr Val Ser Trp Glu Arg Ser Thr Thr Pro Asp Ile Thr
1160                    1165                    1170

Gly Tyr Arg Ile Thr Thr Thr Pro Thr Asn Gly Gln Gln Gly Asn
1175                    1180                    1185

Ser Leu Glu Glu Val Val His Ala Asp Gln Ser Ser Cys Thr Phe
1190                    1195                    1200

Asp Asn Leu Ser Pro Gly Leu Glu Tyr Asn Val Ser Val Tyr Thr
1205                    1210                    1215

Val Lys Asp Asp Lys Glu Ser Val Pro Ile Ser Asp Thr Ile Ile
1220                    1225                    1230

Pro Glu Val Pro Gln Leu Thr Asp Leu Ser Phe Val Asp Ile Thr
1235                    1240                    1245

Asp Ser Ser Ile Gly Leu Arg Trp Thr Pro Leu Asn Ser Ser Thr
1250                    1255                    1260

Ile Ile Gly Tyr Arg Ile Thr Val Val Ala Ala Gly Glu Gly Ile
1265                    1270                    1275

Pro Ile Phe Glu Asp Phe Val Asp Ser Ser Val Gly Tyr Tyr Thr
1280                    1285                    1290

Val Thr Gly Leu Glu Pro Gly Ile Asp Tyr Asp Ile Ser Val Ile
1295                    1300                    1305

Thr Leu Ile Asn Gly Gly Glu Ser Ala Pro Thr Thr Leu Thr Gln
1310                    1315                    1320

Gln Thr Ala Val Pro Pro Pro Thr Asp Leu Arg Phe Thr Asn Ile
1325                    1330                    1335

Gly Pro Asp Thr Met Arg Val Thr Trp Ala Pro Pro Pro Ser Ile
1340                    1345                    1350

Asp Leu Thr Asn Phe Leu Val Arg Tyr Ser Pro Val Lys Asn Glu
1355                    1360                    1365

Glu Asp Val Ala Glu Leu Ser Ile Ser Pro Ser Asp Asn Ala Val
1370                    1375                    1380

Val Leu Thr Asn Leu Leu Pro Gly Thr Glu Tyr Val Val Ser Val
1385                    1390                    1395

Ser Ser Val Tyr Glu Gln His Glu Ser Thr Pro Leu Arg Gly Arg
1400                    1405                    1410

Gln Lys Thr Gly Leu Asp Ser Pro Thr Gly Ile Asp Phe Ser Asp
1415                    1420                    1425

Ile Thr Ala Asn Ser Phe Thr Val His Trp Ile Ala Pro Arg Ala
1430                    1435                    1440

Thr Ile Thr Gly Tyr Arg Ile Arg His His Pro Glu His Phe Ser
1445                    1450                    1455

Gly Arg Pro Arg Glu Asp Arg Val Pro His Ser Arg Asn Ser Ile

-continued

```
            1460               1465                1470
Thr Leu Thr Asn Leu Thr Pro Gly Thr Glu Tyr Val Val Ser Ile
    1475                1480                1485

Val Ala Leu Asn Gly Arg Glu Glu Ser Pro Leu Leu Ile Gly Gln
    1490                1495                1500

Gln Ser Thr Val Ser Asp Val Pro Arg Asp Leu Glu Val Val Ala
    1505                1510                1515

Ala Thr Pro Thr Ser Leu Leu Ile Ser Trp Asp Ala Pro Ala Val
    1520                1525                1530

Thr Val Arg Tyr Tyr Arg Ile Thr Tyr Gly Glu Thr Gly Gly Asn
    1535                1540                1545

Ser Pro Val Gln Glu Phe Thr Val Pro Gly Ser Lys Ser Thr Ala
    1550                1555                1560

Thr Ile Ser Gly Leu Lys Pro Gly Val Asp Tyr Thr Ile Thr Val
    1565                1570                1575

Tyr Ala Val Thr Gly Arg Gly Asp Ser Pro Ala Ser Ser Lys Pro
    1580                1585                1590

Ile Ser Ile Asn Tyr Arg Thr Glu Ile Asp Lys Pro Ser Gln Met
    1595                1600                1605

Gln Val Thr Asp Val Gln Asp Asn Ser Ile Ser Val Lys Trp Leu
    1610                1615                1620

Pro Ser Ser Ser Pro Val Thr Gly Tyr Arg Val Thr Thr Thr Pro
    1625                1630                1635

Lys Asn Gly Pro Gly Pro Thr Lys Thr Lys Thr Ala Gly Pro Asp
    1640                1645                1650

Gln Thr Glu Met Thr Ile Glu Gly Leu Gln Pro Thr Val Glu Tyr
    1655                1660                1665

Val Val Ser Val Tyr Ala Gln Asn Pro Ser Gly Glu Ser Gln Pro
    1670                1675                1680

Leu Val Gln Thr Ala Val Thr Asn Ile Asp Arg Pro Lys Gly Leu
    1685                1690                1695

Ala Phe Thr Asp Val Asp Val Asp Ser Ile Lys Ile Ala Trp Glu
    1700                1705                1710

Ser Pro Gln Gly Gln Val Ser Arg Tyr Arg Val Thr Tyr Ser Ser
    1715                1720                1725

Pro Glu Asp Gly Ile His Glu Leu Phe Pro Ala Pro Asp Gly Glu
    1730                1735                1740

Glu Asp Thr Ala Glu Leu Gln Gly Leu Arg Pro Gly Ser Glu Tyr
    1745                1750                1755

Thr Val Ser Val Val Ala Leu His Asp Asp Met Glu Ser Gln Pro
    1760                1765                1770

Leu Ile Gly Thr Gln Ser Thr Ala Ile Pro Ala Pro Thr Asp Leu
    1775                1780                1785

Lys Phe Thr Gln Val Thr Pro Thr Ser Leu Ser Ala Gln Trp Thr
    1790                1795                1800

Pro Pro Asn Val Gln Leu Thr Gly Tyr Arg Val Arg Val Thr Pro
    1805                1810                1815

Lys Glu Lys Thr Gly Pro Met Lys Glu Ile Asn Leu Ala Pro Asp
    1820                1825                1830

Ser Ser Ser Val Val Val Ser Gly Leu Met Val Ala Thr Lys Tyr
    1835                1840                1845

Glu Val Ser Val Tyr Ala Leu Lys Asp Thr Leu Thr Ser Arg Pro
    1850                1855                1860
```

```
Ala Gln Gly Val Val Thr Thr Leu Glu Asn Val Ser Pro Pro Arg
    1865            1870                1875

Arg Ala Arg Val Thr Asp Ala Thr Glu Thr Thr Ile Thr Ile Ser
    1880            1885                1890

Trp Arg Thr Lys Thr Glu Thr Ile Thr Gly Phe Gln Val Asp Ala
    1895            1900                1905

Val Pro Ala Asn Gly Gln Thr Pro Ile Gln Arg Thr Ile Lys Pro
    1910            1915                1920

Asp Val Arg Ser Tyr Thr Ile Thr Gly Leu Gln Pro Gly Thr Asp
    1925            1930                1935

Tyr Lys Ile Tyr Leu Tyr Thr Leu Asn Asp Asn Ala Arg Ser Ser
    1940            1945                1950

Pro Val Val Ile Asp Ala Ser Thr Ala Ile Asp Ala Pro Ser Asn
    1955            1960                1965

Leu Arg Phe Leu Ala Thr Thr Pro Asn Ser Leu Leu Val Ser Trp
    1970            1975                1980

Gln Pro Pro Arg Ala Arg Ile Thr Gly Tyr Ile Ile Lys Tyr Glu
    1985            1990                1995

Lys Pro Gly Ser Pro Pro Arg Glu Val Val Pro Arg Pro Arg Pro
    2000            2005                2010

Gly Val Thr Glu Ala Thr Ile Thr Gly Leu Glu Pro Gly Thr Glu
    2015            2020                2025

Tyr Thr Ile Tyr Val Ile Ala Leu Lys Asn Asn Gln Lys Ser Glu
    2030            2035                2040

Pro Leu Ile Gly Arg Lys Lys Thr Asp Glu Leu Pro Gln Leu Val
    2045            2050                2055

Thr Leu Pro His Pro Asn Leu His Gly Pro Glu Ile Leu Asp Val
    2060            2065                2070

Pro Ser Thr Val Gln Lys Thr Pro Phe Val Thr His Pro Gly Tyr
    2075            2080                2085

Asp Thr Gly Asn Gly Ile Gln Leu Pro Gly Thr Ser Gly Gln Gln
    2090            2095                2100

Pro Ser Val Gly Gln Gln Met Ile Phe Glu Glu His Gly Phe Arg
    2105            2110                2115

Arg Thr Thr Pro Pro Thr Thr Ala Thr Pro Ile Arg His Arg Pro
    2120            2125                2130

Arg Pro Tyr Pro Pro Asn Val Gly Gln Glu Ala Leu Ser Gln Thr
    2135            2140                2145

Thr Ile Ser Trp Ala Pro Phe Gln Asp Thr Ser Glu Tyr Ile Ile
    2150            2155                2160

Ser Cys His Pro Val Gly Thr Asp Glu Glu Pro Leu Gln Phe Arg
    2165            2170                2175

Val Pro Gly Thr Ser Thr Ser Ala Thr Leu Thr Gly Leu Thr Arg
    2180            2185                2190

Gly Ala Thr Tyr Asn Ile Ile Val Glu Ala Leu Lys Asp Gln Gln
    2195            2200                2205

Arg His Lys Val Arg Glu Glu Val Val Thr Val Gly Asn Ser Val
    2210            2215                2220

Asn Glu Gly Leu Asn Gln Pro Thr Asp Asp Ser Cys Phe Asp Pro
    2225            2230                2235

Tyr Thr Val Ser His Tyr Ala Val Gly Asp Glu Trp Glu Arg Met
    2240            2245                2250
```

```
Ser Glu Ser Gly Phe Lys Leu Leu Cys Gln Cys Leu Gly Phe Gly
    2255                2260                2265

Ser Gly His Phe Arg Cys Asp Ser Ser Arg Trp Cys His Asp Asn
    2270                2275                2280

Gly Val Asn Tyr Lys Ile Gly Glu Lys Trp Asp Arg Gln Gly Glu
    2285                2290                2295

Asn Gly Gln Met Met Ser Cys Thr Cys Leu Gly Asn Gly Lys Gly
    2300                2305                2310

Glu Phe Lys Cys Asp Pro His Glu Ala Thr Cys Tyr Asp Asp Gly
    2315                2320                2325

Lys Thr Tyr His Val Gly Glu Gln Trp Gln Lys Glu Tyr Leu Gly
    2330                2335                2340

Ala Ile Cys Ser Cys Thr Cys Phe Gly Gly Gln Arg Gly Trp Arg
    2345                2350                2355

Cys Asp Asn Cys Arg Arg Pro Gly Gly Glu Pro Ser Pro Glu Gly
    2360                2365                2370

Thr Thr Gly Gln Ser Tyr Asn Gln Tyr Ser Gln Arg Tyr His Gln
    2375                2380                2385

Arg Thr Asn Thr Asn Val Asn Cys Pro Ile Glu Cys Phe Met Pro
    2390                2395                2400

Leu Asp Val Gln Ala Asp Arg Glu Asp Ser Arg Glu
    2405                2410                2415

<210> SEQ ID NO 7
<211> LENGTH: 109
<212> TYPE: PRT
<213> ORGANISM: Homo sapiens

<400> SEQUENCE: 7

Ser Leu Gly Ser Leu Thr Ile Ala Glu Pro Ala Met Ile Ala Glu Cys
1               5                   10                  15

Lys Thr Arg Thr Glu Val Phe Glu Ile Ser Arg Arg Leu Ile Asp Arg
            20                  25                  30

Thr Asn Ala Asn Phe Leu Val Trp Pro Pro Cys Val Glu Val Gln Arg
        35                  40                  45

Cys Ser Gly Cys Cys Asn Asn Arg Asn Val Gln Cys Arg Pro Thr Gln
    50                  55                  60

Val Gln Leu Arg Pro Val Gln Val Arg Lys Ile Glu Ile Val Arg Lys
65                  70                  75                  80

Lys Pro Ile Phe Lys Lys Ala Thr Val Thr Leu Glu Asp His Leu Ala
                85                  90                  95

Cys Lys Cys Glu Thr Val Ala Ala Ala Arg Pro Val Thr
            100                 105

<210> SEQ ID NO 8
<211> LENGTH: 2179
<212> TYPE: PRT
<213> ORGANISM: Homo sapiens

<400> SEQUENCE: 8

Gly Val Leu Lys Lys Val Ile Arg His Lys Arg Gln Ser Gly Val Asn
1               5                   10                  15

Ala Thr Leu Pro Glu Glu Asn Gln Pro Val Val Phe Asn His Val Tyr
            20                  25                  30

Asn Ile Lys Leu Pro Val Gly Ser Gln Cys Ser Val Asp Leu Glu Ser
        35                  40                  45
```

```
Ala Ser Gly Glu Lys Asp Leu Ala Pro Pro Ser Glu Pro Ser Glu Ser
    50                  55                  60
Phe Gln Glu His Thr Val Asp Gly Glu Asn Gln Ile Val Phe Thr His
 65                  70                  75                  80
Arg Ile Asn Ile Pro Arg Arg Ala Cys Gly Cys Ala Ala Ala Pro Asp
                 85                  90                  95
Val Lys Glu Leu Leu Ser Arg Leu Glu Glu Leu Glu Asn Leu Val Ser
            100                 105                 110
Ser Leu Arg Glu Gln Cys Thr Ala Gly Ala Gly Cys Cys Leu Gln Pro
        115                 120                 125
Ala Thr Gly Arg Leu Asp Thr Arg Pro Phe Cys Ser Gly Arg Gly Asn
    130                 135                 140
Phe Ser Thr Glu Gly Cys Gly Cys Val Cys Glu Pro Gly Trp Lys Gly
145                 150                 155                 160
Pro Asn Cys Ser Glu Pro Glu Cys Pro Gly Asn Cys His Leu Arg Gly
                165                 170                 175
Arg Cys Ile Asp Gly Gln Cys Ile Cys Asp Asp Gly Phe Thr Gly Glu
            180                 185                 190
Asp Cys Ser Gln Leu Ala Cys Pro Ser Asp Cys Asn Asp Gln Gly Lys
        195                 200                 205
Cys Val Asn Gly Val Cys Ile Cys Phe Glu Gly Tyr Ala Gly Ala Asp
    210                 215                 220
Cys Ser Arg Glu Ile Cys Pro Val Pro Cys Ser Glu Glu His Gly Thr
225                 230                 235                 240
Cys Val Asp Gly Leu Cys Val Cys His Asp Gly Phe Ala Gly Asp Asp
                245                 250                 255
Cys Asn Lys Pro Leu Cys Leu Asn Asn Cys Tyr Asn Arg Gly Arg Cys
            260                 265                 270
Val Glu Asn Glu Cys Val Cys Asp Glu Gly Phe Thr Gly Glu Asp Cys
        275                 280                 285
Ser Glu Leu Ile Cys Pro Asn Asp Cys Phe Asp Arg Gly Arg Cys Ile
    290                 295                 300
Asn Gly Thr Cys Tyr Cys Glu Glu Gly Phe Thr Gly Glu Asp Cys Gly
305                 310                 315                 320
Lys Pro Thr Cys Pro His Ala Cys His Thr Gln Gly Arg Cys Glu Glu
                325                 330                 335
Gly Gln Cys Val Cys Asp Glu Gly Phe Ala Gly Val Asp Cys Ser Glu
            340                 345                 350
Lys Arg Cys Pro Ala Asp Cys His Asn Arg Gly Arg Cys Val Asp Gly
        355                 360                 365
Arg Cys Glu Cys Asp Asp Gly Phe Thr Gly Ala Asp Cys Gly Glu Leu
    370                 375                 380
Lys Cys Pro Asn Gly Cys Ser Gly His Gly Arg Cys Val Asn Gly Gln
385                 390                 395                 400
Cys Val Cys Asp Glu Gly Tyr Thr Gly Glu Asp Cys Ser Gln Leu Arg
                405                 410                 415
Cys Pro Asn Asp Cys His Ser Arg Gly Arg Cys Val Glu Gly Lys Cys
            420                 425                 430
Val Cys Glu Gln Gly Phe Lys Gly Tyr Asp Cys Ser Asp Met Ser Cys
        435                 440                 445
Pro Asn Asp Cys His Gln His Gly Arg Cys Val Asn Gly Met Cys Val
    450                 455                 460
Cys Asp Asp Gly Tyr Thr Gly Glu Asp Cys Arg Asp Arg Gln Cys Pro
```

```
                465                 470                 475                 480
Arg Asp Cys Ser Asn Arg Gly Leu Cys Val Asp Gly Gln Cys Val Cys
                    485                 490                 495

Glu Asp Gly Phe Thr Gly Pro Asp Cys Ala Glu Leu Ser Cys Pro Asn
                500                 505                 510

Asp Cys His Gly Gln Gly Arg Cys Val Asn Gly Gln Cys Val Cys His
            515                 520                 525

Glu Gly Phe Met Gly Lys Asp Cys Lys Glu Gln Arg Cys Pro Ser Asp
        530                 535                 540

Cys His Gly Gln Gly Arg Cys Val Asp Gly Gln Cys Ile Cys His Glu
545                 550                 555                 560

Gly Phe Thr Gly Leu Asp Cys Gly Gln His Ser Cys Pro Ser Asp Cys
                565                 570                 575

Asn Asn Leu Gly Gln Cys Val Ser Gly Arg Cys Ile Cys Asn Glu Gly
                580                 585                 590

Tyr Ser Gly Glu Asp Cys Ser Glu Val Ser Pro Pro Lys Asp Leu Val
            595                 600                 605

Val Thr Glu Val Thr Glu Glu Thr Val Asn Leu Ala Trp Asp Asn Glu
        610                 615                 620

Met Arg Val Thr Glu Tyr Leu Val Val Tyr Thr Pro Thr His Glu Gly
625                 630                 635                 640

Gly Leu Glu Met Gln Phe Arg Val Pro Gly Asp Gln Thr Ser Thr Ile
                645                 650                 655

Ile Gln Glu Leu Glu Pro Gly Val Glu Tyr Phe Ile Arg Val Phe Ala
                660                 665                 670

Ile Leu Glu Asn Lys Lys Ser Ile Pro Val Ser Ala Arg Val Ala Thr
            675                 680                 685

Tyr Leu Pro Ala Pro Glu Gly Leu Lys Phe Lys Ser Ile Lys Glu Thr
        690                 695                 700

Ser Val Glu Val Glu Trp Asp Pro Leu Asp Ile Ala Phe Glu Thr Trp
705                 710                 715                 720

Glu Ile Ile Phe Arg Asn Met Asn Lys Glu Asp Glu Gly Glu Ile Thr
                725                 730                 735

Lys Ser Leu Arg Arg Pro Glu Thr Ser Tyr Arg Gln Thr Gly Leu Ala
                740                 745                 750

Pro Gly Gln Glu Tyr Glu Ile Ser Leu His Ile Val Lys Asn Asn Thr
            755                 760                 765

Arg Gly Pro Gly Leu Lys Arg Val Thr Thr Thr Arg Leu Asp Ala Pro
        770                 775                 780

Ser Gln Ile Glu Val Lys Asp Val Thr Asp Thr Thr Ala Leu Ile Thr
785                 790                 795                 800

Trp Phe Lys Pro Leu Ala Glu Ile Asp Gly Ile Glu Leu Thr Tyr Gly
                805                 810                 815

Ile Lys Asp Val Pro Gly Asp Arg Thr Thr Ile Asp Leu Thr Glu Asp
                820                 825                 830

Glu Asn Gln Tyr Ser Ile Gly Asn Leu Lys Pro Asp Thr Glu Tyr Glu
            835                 840                 845

Val Ser Leu Ile Ser Arg Arg Gly Asp Met Ser Ser Asn Pro Ala Lys
        850                 855                 860

Glu Thr Phe Thr Thr Gly Leu Asp Ala Pro Arg Asn Leu Arg Arg Val
865                 870                 875                 880

Ser Gln Thr Asp Asn Ser Ile Thr Leu Glu Trp Arg Asn Gly Lys Ala
                885                 890                 895
```

```
Ala Ile Asp Ser Tyr Arg Ile Lys Tyr Ala Pro Ile Ser Gly Gly Asp
            900                 905                 910

His Ala Glu Val Asp Val Pro Lys Ser Gln Gln Ala Thr Thr Lys Thr
            915                 920                 925

Thr Leu Thr Gly Leu Arg Pro Gly Thr Glu Tyr Gly Ile Gly Val Ser
            930                 935                 940

Ala Val Lys Glu Asp Lys Glu Ser Asn Pro Ala Thr Ile Asn Ala Ala
945                 950                 955                 960

Thr Glu Leu Asp Thr Pro Lys Asp Leu Gln Val Ser Glu Thr Ala Glu
            965                 970                 975

Thr Ser Leu Thr Leu Leu Trp Lys Thr Pro Leu Ala Lys Phe Asp Arg
            980                 985                 990

Tyr Arg Leu Asn Tyr Ser Leu Pro Thr Gly Gln Trp Val Gly Val Gln
            995                 1000                1005

Leu Pro Arg Asn Thr Thr Ser Tyr Val Leu Arg Gly Leu Glu Pro
        1010                1015                1020

Gly Gln Glu Tyr Asn Val Leu Leu Thr Ala Glu Lys Gly Arg His
        1025                1030                1035

Lys Ser Lys Pro Ala Arg Val Lys Ala Ser Thr Glu Gln Ala Pro
        1040                1045                1050

Glu Leu Glu Asn Leu Thr Val Thr Glu Val Gly Trp Asp Gly Leu
        1055                1060                1065

Arg Leu Asn Trp Thr Ala Ala Asp Gln Ala Tyr Glu His Phe Ile
        1070                1075                1080

Ile Gln Val Gln Glu Ala Asn Lys Val Glu Ala Ala Arg Asn Leu
        1085                1090                1095

Thr Val Pro Gly Ser Leu Arg Ala Val Asp Ile Pro Gly Leu Lys
        1100                1105                1110

Ala Ala Thr Pro Tyr Thr Val Ser Ile Tyr Gly Val Ile Gln Gly
        1115                1120                1125

Tyr Arg Thr Pro Val Leu Ser Ala Glu Ala Ser Thr Gly Glu Thr
        1130                1135                1140

Pro Asn Leu Gly Glu Val Val Val Ala Glu Val Gly Trp Asp Ala
        1145                1150                1155

Leu Lys Leu Asn Trp Thr Ala Pro Glu Gly Ala Tyr Glu Tyr Phe
        1160                1165                1170

Phe Ile Gln Val Gln Glu Ala Asp Thr Val Glu Ala Ala Gln Asn
        1175                1180                1185

Leu Thr Val Pro Gly Gly Leu Arg Ser Thr Asp Leu Pro Gly Leu
        1190                1195                1200

Lys Ala Ala Thr His Tyr Thr Ile Thr Ile Arg Gly Val Thr Gln
        1205                1210                1215

Asp Phe Ser Thr Thr Pro Leu Ser Val Glu Val Leu Thr Glu Glu
        1220                1225                1230

Val Pro Asp Met Gly Asn Leu Thr Val Thr Glu Val Ser Trp Asp
        1235                1240                1245

Ala Leu Arg Leu Asn Trp Thr Thr Pro Asp Gly Thr Tyr Asp Gln
        1250                1255                1260

Phe Thr Ile Gln Val Gln Glu Ala Asp Gln Val Glu Glu Ala His
        1265                1270                1275

Asn Leu Thr Val Pro Gly Ser Leu Arg Ser Met Glu Ile Pro Gly
        1280                1285                1290
```

-continued

| | | | | | | | | | | | |
|---|---|---|---|---|---|---|---|---|---|---|---|
| Leu | Arg | Ala | Gly | Thr | Pro | Tyr | Thr | Val | Thr | Leu | His | Gly | Glu | Val |
| | 1295 | | | | 1300 | | | | | 1305 | | | | |

Leu Arg Ala Gly Thr Pro Tyr Thr Val Thr Leu His Gly Glu Val
    1295                1300                  1305

Arg Gly His Ser Thr Arg Pro Leu Ala Val Glu Val Val Thr Glu
    1310                1315                  1320

Asp Leu Pro Gln Leu Gly Asp Leu Ala Val Ser Glu Val Gly Trp
    1325                1330                  1335

Asp Gly Leu Arg Leu Asn Trp Thr Ala Ala Asp Asn Ala Tyr Glu
    1340                1345                  1350

His Phe Val Ile Gln Val Gln Glu Val Asn Lys Val Glu Ala Ala
    1355                1360                  1365

Gln Asn Leu Thr Leu Pro Gly Ser Leu Arg Ala Val Asp Ile Pro
    1370                1375                  1380

Gly Leu Glu Ala Ala Thr Pro Tyr Arg Val Ser Ile Tyr Gly Val
    1385                1390                  1395

Ile Arg Gly Tyr Arg Thr Pro Val Leu Ser Ala Glu Ala Ser Thr
    1400                1405                  1410

Ala Lys Glu Pro Glu Ile Gly Asn Leu Asn Val Ser Asp Ile Thr
    1415                1420                  1425

Pro Glu Ser Phe Asn Leu Ser Trp Met Ala Thr Asp Gly Ile Phe
    1430                1435                  1440

Glu Thr Phe Thr Ile Glu Ile Ile Asp Ser Asn Arg Leu Leu Glu
    1445                1450                  1455

Thr Val Glu Tyr Asn Ile Ser Gly Ala Glu Arg Thr Ala His Ile
    1460                1465                  1470

Ser Gly Leu Pro Pro Ser Thr Asp Phe Ile Val Tyr Leu Ser Gly
    1475                1480                  1485

Leu Ala Pro Ser Ile Arg Thr Lys Thr Ile Ser Ala Thr Ala Thr
    1490                1495                  1500

Thr Glu Ala Leu Pro Leu Leu Glu Asn Leu Thr Ile Ser Asp Ile
    1505                1510                  1515

Asn Pro Tyr Gly Phe Thr Val Ser Trp Met Ala Ser Glu Asn Ala
    1520                1525                  1530

Phe Asp Ser Phe Leu Val Thr Val Val Asp Ser Gly Lys Leu Leu
    1535                1540                  1545

Asp Pro Gln Glu Phe Thr Leu Ser Gly Thr Gln Arg Lys Leu Glu
    1550                1555                  1560

Leu Arg Gly Leu Ile Thr Gly Ile Gly Tyr Glu Val Met Val Ser
    1565                1570                  1575

Gly Phe Thr Gln Gly His Gln Thr Lys Pro Leu Arg Ala Glu Ile
    1580                1585                  1590

Val Thr Glu Ala Glu Pro Glu Val Asp Asn Leu Leu Val Ser Asp
    1595                1600                  1605

Ala Thr Pro Asp Gly Phe Arg Leu Ser Trp Thr Ala Asp Glu Gly
    1610                1615                  1620

Val Phe Asp Asn Phe Val Leu Lys Ile Arg Asp Thr Lys Lys Gln
    1625                1630                  1635

Ser Glu Pro Leu Glu Ile Thr Leu Leu Ala Pro Glu Arg Thr Arg
    1640                1645                  1650

Asp Ile Thr Gly Leu Arg Glu Ala Thr Glu Tyr Glu Ile Glu Leu
    1655                1660                  1665

Tyr Gly Ile Ser Lys Gly Arg Arg Ser Gln Thr Val Ser Ala Ile
    1670                1675                  1680

Ala Thr Thr Ala Met Gly Ser Pro Lys Glu Val Ile Phe Ser Asp

-continued

```
            1685                1690                1695
Ile Thr Glu Asn Ser Ala Thr Val Ser Trp Arg Ala Pro Thr Ala
    1700                1705                1710
Gln Val Glu Ser Phe Arg Ile Thr Tyr Val Pro Ile Thr Gly Gly
    1715                1720                1725
Thr Pro Ser Met Val Thr Val Asp Gly Thr Lys Thr Gln Thr Arg
    1730                1735                1740
Leu Val Lys Leu Ile Pro Gly Val Glu Tyr Leu Val Ser Ile Ile
    1745                1750                1755
Ala Met Lys Gly Phe Glu Glu Ser Glu Pro Val Ser Gly Ser Phe
    1760                1765                1770
Thr Thr Ala Leu Asp Gly Pro Ser Gly Leu Val Thr Ala Asn Ile
    1775                1780                1785
Thr Asp Ser Glu Ala Leu Ala Arg Trp Gln Pro Ala Ile Ala Thr
    1790                1795                1800
Val Asp Ser Tyr Val Ile Ser Tyr Thr Gly Glu Lys Val Pro Glu
    1805                1810                1815
Ile Thr Arg Thr Val Ser Gly Asn Thr Val Glu Tyr Ala Leu Thr
    1820                1825                1830
Asp Leu Glu Pro Ala Thr Glu Tyr Thr Leu Arg Ile Phe Ala Glu
    1835                1840                1845
Lys Gly Pro Gln Lys Ser Ser Thr Ile Thr Ala Lys Phe Thr Thr
    1850                1855                1860
Asp Leu Asp Ser Pro Arg Asp Leu Thr Ala Thr Glu Val Gln Ser
    1865                1870                1875
Glu Thr Ala Leu Leu Thr Trp Arg Pro Pro Arg Ala Ser Val Thr
    1880                1885                1890
Gly Tyr Leu Leu Val Tyr Glu Ser Val Asp Gly Thr Val Lys Glu
    1895                1900                1905
Val Ile Val Gly Pro Asp Thr Thr Ser Tyr Ser Leu Ala Asp Leu
    1910                1915                1920
Ser Pro Ser Thr His Tyr Thr Ala Lys Ile Gln Ala Leu Asn Gly
    1925                1930                1935
Pro Leu Arg Ser Asn Met Ile Gln Thr Ile Phe Thr Thr Ile Gly
    1940                1945                1950
Leu Leu Tyr Pro Phe Pro Lys Asp Cys Ser Gln Ala Met Leu Asn
    1955                1960                1965
Gly Asp Thr Thr Ser Gly Leu Tyr Thr Ile Tyr Leu Asn Gly Asp
    1970                1975                1980
Lys Ala Glu Ala Leu Glu Val Phe Cys Asp Met Thr Ser Asp Gly
    1985                1990                1995
Gly Gly Trp Ile Val Phe Leu Arg Arg Lys Asn Gly Arg Glu Asn
    2000                2005                2010
Phe Tyr Gln Asn Trp Lys Ala Tyr Ala Ala Gly Phe Gly Asp Arg
    2015                2020                2025
Arg Glu Glu Phe Trp Leu Gly Leu Asp Asn Leu Asn Lys Ile Thr
    2030                2035                2040
Ala Gln Gly Gln Tyr Glu Leu Arg Val Asp Leu Arg Asp His Gly
    2045                2050                2055
Glu Thr Ala Phe Ala Val Tyr Asp Lys Phe Ser Val Gly Asp Ala
    2060                2065                2070
Lys Thr Arg Tyr Lys Leu Lys Val Glu Gly Tyr Ser Gly Thr Ala
    2075                2080                2085
```

```
Gly Asp Ser Met Ala Tyr His Asn Gly Arg Ser Phe Ser Thr Phe
    2090            2095                2100

Asp Lys Asp Thr Asp Ser Ala Ile Thr Asn Cys Ala Leu Ser Tyr
    2105            2110                2115

Lys Gly Ala Phe Trp Tyr Arg Asn Cys His Arg Val Asn Leu Met
    2120            2125                2130

Gly Arg Tyr Gly Asp Asn Asn His Ser Gln Gly Val Asn Trp Phe
    2135            2140                2145

His Trp Lys Gly His Glu His Ser Ile Gln Phe Ala Glu Met Lys
    2150            2155                2160

Leu Arg Pro Ser Asn Phe Arg Asn Leu Glu Gly Arg Arg Lys Arg
    2165            2170                2175

Ala
```

COLONY FORMING MEDIUM AND USE THEREOF

CROSS REFERENCE TO RELATED APPLICATIONS

This application is the U.S. national phase application, pursuant to 35 U.S.C. § 371, of PCT International Application Ser. No.: PCT/AU2017/050228, filed Mar. 14, 2017, designating the United States and published in English, which claims the benefit of the following Australian Patent Application Nos.: 2016900983, filed 16 Mar. 2016; 2016904039, filed 5 Oct. 2016 and 2017900318, filed 2 Feb. 2017, each of which is incorporated by reference in its entirety.

FIELD

The invention relates to a method of differentiating a human pluripotent stem cell (PSC) into a mesenchymal stem cell (MSC), and to compositions useful for such differentiation. The invention also relates to a MSC differentiated by the method, a population of the MSCs differentiated by the method, and to methods and uses of the MSC or population of MSCs.

BACKGROUND

Pluripotent stem cells (PSCs), in particular human PSCs, which include Embryonic Stem Cells (ESCs) and induced Pluripotent Stem Cells (iPSCs), provide the opportunity to study human development in vitro and develop novel cell-based therapeutic products. The use of PSCs as a starting material for the manufacture of therapeutic products has several advantages, including the potential to manufacture a virtually limitless number of cells from a single cell bank, as a result of the capacity of PSCs to reproduce indefinitely in vitro, and to differentiate into any cell type.

Most protocols differentiate human PSCs grown on mouse embryonic fibroblasts (MEFs) or MATRIGEL®, a solubilised basement membrane preparation extracted from the Engelbreth-Holm-Swarm (EHS) mouse sarcoma. A chemically-defined, xenogen-free medium and matrix for human PSC-derivation and maintenance has been described. A chemically-defined, xenogen-free directed differentiation protocol for deriving hematopoietic progenitors from human PSCs has also been described in US 2014/0273211 A1.

In particular, US 2014/0273211 A1 describes a method for differentiating human pluripotent stem cells comprising: (a) providing human pluripotent stem cells; and (b) culturing the human pluripotent stem cells under hypoxic conditions in a cell culture medium comprising FGF2, BMP4, Activin A, and LiCl for a period of about two days to form a cell population of $^{EMH}$lin-KDR+APLNR+PDGFRalpha+ primitive mesoderm cells with mesenchymoangioblast potential. US 2014/0273211 A1 also describes a xenogen-free culture medium for differentiating human pluripotent stem cells, comprising IF9S medium supplemented with: about 50 to about 250 ng/mL BMP4; about 10 to about 15 ng/mL Activin A; about 10 to about 50 ng/mL FGF2; and about 1 mM to about 2 mM LiCl.

However, US 2014/0273211 A1 is silent in respect of any improved mesenchymal-colony forming medium (M-CFM).

Mesenchymal stem cells (MSCs) hold significant promise as a cell therapy and are currently in clinical trials for treating numerous diseases, including graft-versus host disease. Induced pluripotent stem cell (iPSC)-derived MSCs have a unique advantage over directly sourced MSCs, i.e. derived from tissues such as bone marrow, umbilical cord blood, adipose tissue, because in vitro expansion of iPSCs can provide a virtually unlimited supply of MSCs.

Nevertheless, despite their promise, there remain challenges in producing MSCs in vitro, for example scaling up production from laboratory scale to good manufacturing practice (GMP) scale, which for any biological product is neither facile nor necessarily predictable, as will be appreciated in the art.

It follows that there is a need for improved and scalable methods for differentiating PSCs, including iPSCs, into MSCs.

Any publications mentioned in this specification are herein incorporated by reference. However, if any publication is referred to herein, such reference does not constitute an admission that the publication forms a part of the common general knowledge in the art in Australia or any other country.

SUMMARY

The inventors have identified a specific composition for a differentiation medium that differentiates PSCs to MSCs, wherein such MSCs possess superior immunosuppressive properties relative to MSCs differentiated in the absence of the differentiation medium disclosed herein. Furthermore, the method is applicable to GMP-scale, i.e. a scale sufficient to supply MSCs for therapeutic use.

In a first aspect, the invention provides a MSC expressing the miR-145-5p, miR-181b-5p and miR-214-3p, but not miR-127-3p or miR-299-5p.

In one embodiment, the MSC has a CD73+CD105+CD90+CD146+CD44+CD10+CD31−CD45− phenotype.

In a second aspect, the invention provides a method for producing an MSC, the method comprising:
 (a) culturing a primitive mesoderm cell in a M-CFM comprising LiCl and FGF2, but excluding PDGF, under normoxic conditions for sufficient time for a mesenchymal colony to form; and
 (b) culturing the mesenchymal colony of (a) adherently to produce the MSC,
 wherein the MSC of (b) has superior T-cell immunosuppressive properties relative to an MSC not produced in said M-CFM.

In one embodiment, the primitive mesodermal cell is a primitive mesodermal cell with mesenchymoangioblast (MCA) potential. In one embodiment, the primitive mesodermal cell with MCA potential has a $^{EMH}$lin−KDR+APLNR+PDGFRalpha+ phenotype.

In one embodiment, sufficient time for the mesenchymal colony to be produced is about 8 days to about 14 days. In one embodiment, sufficient time for the mesenchymal colony to be produced is about 12 days.

In one embodiment, T-cell immunosuppressive properties of the MSC are determined relative to an MSC produced by a method comprising:
 (a') culturing a primitive mesodermal cell in a medium comprising FGF2 and optionally PDGF, but excluding LiCl, under normoxic conditions for sufficient time for a mesenchymal colony to form; and
 (b') culturing the mesenchymel colony of (a') adherently to produce the MSC.

In one embodiment, T-cell immunosuppressive properties of the MSC are determined relative to an MSC produced from a primitive mesodermal cell differentiated from a PSC in a differentiation medium comprising FGF2, BMP4, Activin A, and LiCl under hypoxic conditions for about two days.

In a third aspect, the invention provides an MSC produced by the method of the second aspect.

In a fourth aspect, the invention provides a population of MSCs, comprising the MSC of the first or third aspect. The population of MSCs In a fifth aspect, the invention provides a therapeutic composition comprising the MSC of the first or third aspect, or the population of MSCs of the fourth aspect.

In a sixth aspect, the invention provides a kit comprising a container containing the MSC of the first or third aspect, the population of MSCs of the fourth aspect, or the therapeutic composition of the fifth aspect.

In a seventh aspect, the invention provides a mesenchymal colony forming medium (M-CFM), comprising about 1 mM LiCl, and about 5 ng/mL to about 100 ng/mL FGF2, or about 10 ng/mL to about 50 ng/mL FGF2, about 10 ng/mL FGF2, or about 20 ng/mL FGF2, but excluding PDGF.

In an eighth aspect, the invention provides a composition comprising LiCl and FGF2, but excluding PDGF, that, when admixed with a liquid comprising water, produces a M-CFM comprising about 1 mM LiCl, and about 5 ng/mL to about 100 ng/mL FGF2, or about 10 ng/mL to about 50 ng/mL FGF2, about 10 ng/mL FGF2, or about 20 ng/mL FGF2, but excluding PDGF.

In a ninth aspect, the invention provides use of the MSC of the first or third aspect or the population of MSCs of the fourth aspect in the manufacture of a medicament for treating or preventing a condition such as bone cysts, bone neoplasms, fractures, cartilage defects, osteoarthritis, ligament injury, osteogenesis imperfecta, osteonecrosis, osteoporosis, aplastic anaemia, graft versus host disease (GvHD), myelodysplastic syndrome; Type 1 diabetes, Type 2 diabetes, autoimmune hepatitis, liver cirrhosis, liver failure, dilated cardiomyopathy, heart failure, myocardial infarction, myocardial ischemia, Crohn's disease, ulcerative colitis, burns, epidermolysis bullosa, lupus erythematosus, rheumatoid arthritis, Sjogren's disease, systemic sclerosis, bronchopulmonary dysplasia, chronic obstructive airways disease, emphysema, pulmonary fibrosis, amyotrophic lateral sclerosis (ALS), Alzheimer's disease, brain injury, ataxia, degenerative disc disease, multiple system atrophy, multiple sclerosis, Parkinson's disease, retinitis pigmentosa, Romberg's disease, spinal cord injury, stroke, muscular dystrophy, limb ischaemia, kidney injury, lupus nephritis, endometriosis and complications of bone marrow or solid organ transplantation.

In a tenth aspect, the invention provides a method for treating or preventing a condition such as bone cysts, bone neoplasms, fractures, cartilage defects, osteoarthritis, ligament injury, osteogenesis imperfecta, osteonecrosis, osteoporosis, aplastic anaemia, GvHD, myelodysplastic syndrome; Type 1 diabetes, Type 2 diabetes, autoimmune hepatitis, liver cirrhosis, liver failure, dilated cardiomyopathy, heart failure, myocardial infarction, myocardial ischemia, Crohn's disease, ulcerative colitis, burns, epidermolysis bullosa, lupus erythematosus, rheumatoid arthritis, Sjogren's disease, systemic sclerosis, bronchopulmonary dysplasia, chronic obstructive airways disease, emphysema, pulmonary fibrosis, ALS, Alzheimer's disease, brain injury, ataxia, degenerative disc disease, multiple system atrophy, multiple sclerosis, Parkinson's disease, retinitis pigmentosa, Romberg's disease, spinal cord injury, stroke, muscular dystrophy, limb ischaemia, kidney injury, lupus nephritis, endometriosis and complications of bone marrow or solid organ transplantation, the method comprising administering to a subject the MSC of the first or third aspect, the population of MSCs of the fourth aspect, or the therapeutic composition of the fifth aspect.

Also disclosed is a method of differentiating a pluripotent stem cell (PSC) into a mesenchymal stem cell (MSC), the method comprising:
(a) culturing the PSC in a differentiation medium comprising FGF2, BMP4, Activin A, and LiCl under hypoxic conditions for about two days to form a primitive mesoderm cell;
(b) replacing the differentiation medium of (a) with a mesenchymal colony forming medium (M-CFM) Comprising LiCl and FGF2, but excluding PDGF;
(c) culturing the primitive mesoderm cell of (b) in the M-CFM of (b) under normoxic conditions for sufficient time for a mesenchymal colony to form; and
(d) culturing the mesenchymal colony of (c) adherently to produce the MSC,
wherein the MSC has superior T-cell immunosuppressive properties relative to an MSC not produced in said M-CFM.

In one embodiment, the method above further comprises:
(e) expanding the MSC of (d).

In one embodiment, the primitive mesodermal cell is a primitive mesodermal cell with mesenchymoangioblast (MCA) potential. In one embodiment, the primitive mesodermal cell with MCA potential is a $^{EMH}$lin$^-$KDR$^+$APLNR$^+$ PDGFRalpha$^+$ primitive mesoderm cell with MCA potential.

In one embodiment, sufficient time for the mesenchymal colony to be form is about 8 days to about 14 days. In one embodiment, sufficient time for the mesenchymal colony to form is about 12 days.

In one embodiment, T-cell immunosuppress properties of the MSC are determined relative to an MSC produced from a primitive mesodermal cell cultured in a medium comprising FGF2 and optionally PDGF, but excluding LiCl.

In one embodiment, T-cell immunosuppressive properties of the MSC are determined relative to an MSC produced from a primitive mesodermal cell differentiated from a PSC in a differentiation medium comprising FGF2, BMP4, Activin A, and LiCl under hypoxic conditions for about two days.

BRIEF DESCRIPTION OF THE FIGURES

Embodiments of the invention are described below by way of example only with reference to the accompanying figures in which FIG. 1 is an amino acid sequence (SEQ ID NO: 1) representing a polypeptide that as a homodimer is one example of human activin A.

FIG. 2 is an amino acid sequence (SEQ ID NO: 2) representing a polypeptide that as a homodimer is one example of human BMP4. SEQ ID NO: 2 corresponds to amino acids 303 to 408 of an amino acid sequence of a full length BMP4 precursor.

FIG. 3 is an amino acid sequence (SEQ ID NO: 3) representing a polypeptide that is one example of a human type I collagen alpha1 chain. Human type I collagen (collagen I) is a triple helix trimer that in one example has two alpha1 chains represented by SEQ ID NO: 3 and one alpha2 chain. SEQ ID NO: 3 corresponds to amino acids 162 to 1218 of a full length type I collagen alpha1 chain precursor.

FIG. 4 is an amino acid sequence (SEQ ID NO: 4) representing a polypeptide that is one example of a human type IV collagen alpha1 chain. Human type IV collagen (collagen IV) is a triple helix heterotrimer that in one example comprises one alphal chain represented by SEQ ID NO: 4. SEQ ID NO: 4 corresponds to amino acids 173 to 1669 of a full length type IV collagen alpha1 chain precursor.

FIG. 5 is an amino acid sequence (SEQ ID NO: 5) representing a polypeptide that is one example of human FGF2.

FIG. 6 is an amino acid sequence (SEQ ID NO: 6) representing a polypeptide that as a dimer is one example of human fibronectin. SEQ ID NO: 6 corresponds to amino acids 32 to 2446 of a full length fibronectin precursor.

FIG. 7 is an amino acid sequence (SEQ ID NO: 7) representing a polypeptide that as a homodimer is one example of human PDGF (PDGF-BB). SEQ ID NO: 7 corresponds to amino acids 82 to 190 of a full length PDGF subunit B precursor.

FIG. 8 is an amino acid sequence (SEQ ID NO: 8) representing a polypeptide that as a hexamer is one example of human tenascin C. SEQ ID NO: 8 corresponds to amino acids 23 to 2201 of a full length tenascin C precursor.

FIG. 14 shows functional assessment (TTE) and comprises line graphs showing individual assessments and column graphs showing group assessment of fractional shortening (FS) of the infarcted hearts of example 6. In the vehicle group, baseline FS was higher in 1 rat injected with vehicle, but overall, no or minimal change in FS on day 28 compared to day 0 except for 1 rat (mean increase 1.39%). In the BM MSC group, 3/3 rats had worsening FS on day 28 compared to day 0 (mean decrease 2.3%). In the PSC-MSC group, 4/4 rats had increase in FS on day 28 compared to day 0 (mean increase 5.48%).

FIG. 15 comprises photomicrographs showing scar size using picosirius red staining in infarcted hearts of example 6. The images show an obvious reduction in scar size using Picosirius Red Staining in the PSC-MSC treated groups compared to the vehicle and BM-MSC treated groups.

DETAILED DESCRIPTION

Figure 9:
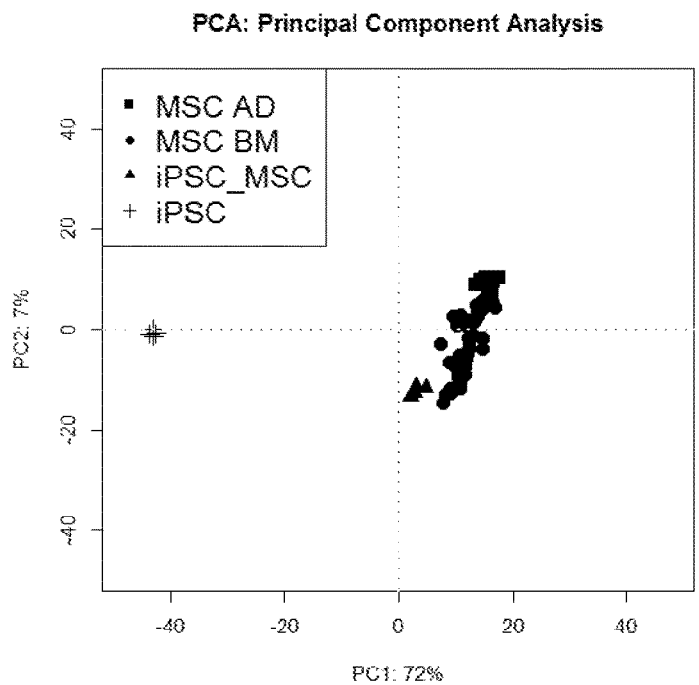
FIG. 9 is a plot representing a principal component analysis of miRNA expression of an MSC of the disclosure and 71 other MSC samples obtained by means other than the present method. AD, adipose (■); BM, bone marrow (♦); iPSC_MSC, MSC of the disclosure (▲); iPSC, iPSC before differentiation to an MSC of the disclosure (+).

The inventors have defined an improved chemically-defined, xenogen-free differentiation protocol, including in particular, an improved chemically-defined, xenogen-free mesenchymal colony forming protocol. Surprisingly, the improved protocols provide MSCs with superior immunosuppressive properties when compared to existing differentiation and mesenchymal colony forming protocols.

In developing the improved chemically-defined, xenogen-free differentiation protocol, including the improved mesenchymal colony forming protocol, the inventors investigated several variables, including: presence/absence of PDGF; presence/absence of LiCl; low/high activin A concentration; and low/high seed density.

PDGF was tested because it was asserted in U.S. Pat. No. 7,615,374 that "PDGF-BB improved growth of mesenchymal cells, but was not essential for colony formation". Surprisingly, however, the inventors describe herein that contrary to this prior teaching, absence of PDGF generated MSCs with superior immunosuppressive properties relative to MSCs generated by differentiation in medium comprising PDGF.

With respect to activin A, the inventors surprisingly found that immunosuppression was improved in MSCs differentiated in medium comprising the lower concentration of activin A relative to the higher concentration of activin A.

LiCl activates Wnt signaling and is included in differentiation medium to improve mesoderm induction during the first 48 hours of differentiation, which is understood in the art.

However, before the present invention, LiCl had not been used in a M-CFM to improve colony formation in clonogenic cultures. Again, this was a surprising advantage of the method disclosed herein.

Accordingly, disclosed herein are methods for differentiating PSCs (e.g. human ESCs or human iPSCs) under defined conditions. Such differentiation provides an MSC or MSC populations that may be a source for functional studies of these lineages as well as a source for clinical therapies.

The ability of MSCs to exert immunomodulatory/immunosuppressive effects, in particular by suppressing T cells, is believed to be central to the therapeutic effects of MSCs in a wide range of conditions, including GvHD, immune disorders including autoimmune disorders, cardiovascular disorders, orthopaedic disorders and rejection of transplanted solid organs. Some specific examples include bone cysts, bone neoplasms, fractures, cartilage defects, osteoarthritis, ligament injury, osteogenesis imperfecta, osteonecrosis, osteoporosis, aplastic anaemia, myelodysplastic syndrome; Type 1 diabetes, Type 2 diabetes, autoimmune hepatitis, liver cirrhosis, liver failure, dilated cardiomyopathy, heart failure, myocardial infarction, myocardial ischemia, Crohn's disease, ulcerative colitis, burns, epidermolysis bullosa, lupus erythematosus, rheumatoid arthritis, Sjogren's disease, systemic sclerosis, bronchopulmonary dysplasia, chronic obstructive airways disease, emphysema, pulmonary fibrosis, ALS, Alzheimer's disease, brain injury, ataxia, degenerative disc disease, multiple system atrophy, multiple sclerosis, Parkinson's disease, retinitis pigmentosa, Romberg's disease, spinal cord injury, stroke, muscular dystrophy, limb ischaemia, kidney injury, lupus nephritis, endometriosis and complications of bone marrow or solid organ transplantation, MSCs are thought to perform a critical role in injury healing, and have been shown to be effective in treating tissue injury and degenerative diseases, including in the digestive system, for example in liver cirrhosis and liver failure, in the musculoskeletal system, in periodontal tissue, in diabetic critical limb ischemia, in osteonecrosis, in burn-related disorders, in myocardial infarction, in cornea damage, in the brain, in the spinal cord, in the lungs, and in treating radiation exposure.

MSCs have shown therapeutic outcomes in immune disorders, including graft-versus-host disease, systemic lupus erythematosus (SLE), Crohn's disease, multiple system atrophy, multiple sclerosis, amyotrophic lateral sclerosis, and stroke.

MSCs have been shown to exert immunosuppressive activities against T cells, B cells, dendritic cells, macrophages, and natural killer cells. While not wishing to be bound by theory, the underlying mechanisms may comprise immunosuppressive mediators, for example nitric oxide, indoleamine 2,3, dioxygenase, prostaglandin E2, tumour necrosis factor-inducible gene 6 protein, CCL-2, and programmed death ligand 1. These mediators are expressed at a low level until stimulated, for example by an inflammatory cytokines, such as IFNγ, TNFα, and IL-17.

In some embodiments, MSCs of the disclosure may be engrafted into damaged tissues following administration and migration.

MSCs may be administered systemically or peripherally, for example by routes including intravenous (IV), intra-arterial, intramuscular, intraperitoneal, intracerobrospinal, subcutaneous (SC), intra-articular, intrasynovial, intrathecal, intracoronary, transendocardial, surgical implantation, topical and inhalation (e.g. intrapulmonary). MSCs may be administered in combination with a scaffold of biocompatible material.

MSCs may be administered before, during or after injury, disorder or disease progression. In one embodiment, MSCs are administered during inflammation. MSCs may be administered (a) as a preventative measure, (b) as soon as the relevant condition has been diagnosed, (c) when other treatments fail, and/or (d) when a condition advances to a pre-defined degree of severity.

In one embodiment, MSCs are pre-treated prior to administration. Pre-treatment may be with a growth factor or by gene editing, for example, where a growth factor may prime the MSC and gene editing may confer a new therapeutic property on the MSC.

Unless defined otherwise in this specification, technical and scientific terms used herein have the same meaning as commonly understood by the person skilled in the art to which this invention belongs and by reference to published texts.

It is to be noted that the term "a" or "an" refers to one or more, for example, "a molecule," is understood to represent one or more molecules. As such, the terms "a" or "an", "one or more," and "at least one" may be used interchangeably herein.

In the claims which follow and in the description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The term "about" as used herein contemplates a range of values for a given number of ±25% the magnitude of that number. In other embodiments, the term "about" contemplates a range of values for a given number of ±20%, ±15%, ±10%, or ±5% the magnitude of that number. For example, in one embodiment, "about 3 grams" indicates a value of 2.7 to 3.3 grams (i.e. 3 grams ±10%), and the like.

Similarly, while differentiation processes include ordered, sequential events, the timing of the events may be varied by at least 25%. For example, while a particular step may be disclosed in one embodiment as lasting one day, the event may last for more or less than one day. For example, "one day" may include a period of about 18 to about 30 hours. In other embodiments, periods of time may vary by ±20%, ±15%, ±10%, or ±5% of that period of time. Periods of time indicated that are multiple day periods may be multiples of "one day," such as, for example, two days may span a period of about 36 to about 60 hours, and the like. In another embodiment, time variation may be lessened, for example, where day 2 is 48±3 hours from day 0; day 4 is 96±3 hours from day 0, and day 5 is 120 hours±3 hours from day 0.

As used herein, "pluripotent stem cell" or "PSC" refers to a cell that has the ability to reproduce itself indefinitely, and to differentiate into any other cell type. There are two main types of pluripotent stem cell: embryonic stem cells (ESCs) and induced pluripotent stem cells (iPSCs).

As used herein, "embryonic stem cell" or "ESC" refers to a cell isolated from a five to seven day-old embryo donated with consent by patients who have completed in vitro fertilisation therapy, and have surplus embryos. The use of ESCs has been hindered to some extent by ethical concerns about the extraction of cells from human embryos.

Suitable human PSCs include H1 and H9 human embryonic stem cells.

As used herein, "induced pluripotent stem cell" or "iPSC" refers to an ESC-like cell derived from adult cells. iPSCs have very similar characteristics to ESCs, but avoid the ethical concerns associated with ESCs, since iPSCs are not derived from embryos. Instead, iPSCs are typically derived from fully differentiated adult cells that have been "reprogrammed" back into a pluripotent state.

Suitable human iPSCs include, but are not limited to, iPSC 19-9-7T, MIRJT6i-mND1-4 and MIRJT7i-mND2-0 derived from fibroblasts and iPSC BM119-9 derived from bone marrow mononuclear cells. Other suitable iPSCs may be obtained from Cellular Dynamics International (CDI; Nasdaq: ICEL) Madison, Wis., USA.

In some embodiments, the PSCs are plated at an initial density of about 5000 cells/cm$^2$ to about 15,000 cells/cm$^2$, e.g., 6000 cells/cm$^2$, 7000 cells/cm$^2$, 8000 cells/cm$^2$, 9000 cells/cm$^2$, 10,000 cells/cm$^2$, 11,000 cells/cm$^2$, 12,000 cells/cm$^2$, 13,000 cells/cm$^2$, or 14,000 cells/cm$^2$.

In one embodiment, sufficient time for the mesenchymal colony to be produced is about 8 days to about 14 days. In one embodiment, sufficient time for the mesenchymal colony to be produced is about 10 days to about 14 days. In one embodiment, sufficient time for the mesenchymal colony to be produced is about 11 days to about 13 days. In one embodiment, sufficient time for the mesenchymal colony to be produced is about 8 days, about 9 days, about 10 days, about 11 days, about 13 days, or about 14 days. In one embodiment, sufficient time for the mesenchymal colony to be produced is about 12 days.

As used herein, "$^{EMH}$lin$^-$KDR$^+$APLNR$^+$PDGFRalpha$^+$ primitive mesoderm cell with mesenchymoangioblast (MCA) potential" refers to a cell expressing typical primitive streak and lateral plate/extraembryonic mesoderm genes. These cells have potential to form mesenchymoangioblast (MCA) and hemangioblast colonies in serum-free medium in response to FGF2. According to the method of present invention, these cells become mesenchymal stem cells (MSCs).

The term $^{EMH}$lin$^-$ denotes lack of expression of CD31, VE-cadherin endothelial markers, CD73 and Cd105 mesenchymal/endothelial markers, and CD43 and CD45 hematopoietic markers.

As used herein, "mesenchyme" or "mesenchymal" refers to to embryonic connective tissue that is derived from the mesoderm and that differentiates into hematopoietic tissue (lymphatic and circulatory systems) and connective tissue, such as bone and cartilage. However, MSCs do not differentiate into hematopoietic cells.

As used herein, "mesenchymal colony" refers to CD73- mesenchymal progenitors that precede true MSCs. Additional adherent culture of mesenchymal colonies, e.g. on fibronectin/collagen-coated plates, is required to produce CD73+ MSCs.

As used herein, "mesenchymal stem cell" or "MSC" refers to a particular type of stem cell that may be isolated from a wide range of tissues, including bone marrow, adipose tissue (fat), placenta and umbilical cord blood. MSCs are also known as "mesenchymal stromal cells". According to the method of present invention, MSCs are formed from $^{EMH}$lin$^-$KDR$^+$APLNR$^+$PDGFRalpha$^+$ primitive mesoderm cells with mesenchymoangioblast (MCA) potential.

MSCs secrete bioactive molecules such as cytokines, chemokines and growth factors and have the ability to modulate the immune system. MSCs have been shown to facilitate regeneration and effects on the immune system without relying upon engraftment. In other words, the MSCs themselves do not necessarily become incorporated into the host—rather, they exert their effects and are then eliminated within a short period of time. However, MSCs may be engrafted.

Therapeutic MSCs can be either "autologous" or "allogeneic". As used herein, "autologous" means a patient is treated with their own cells isolated from bone marrow or adipose tissue, for example, whereas "allogeneic" means that cells from a donor are used to treat other people. According to the present disclosure, allogeneic MSCs are derived from a donor via an iPSC.

Allogeneic MSCs have not been shown to cause immune reactions in other people, so they do not require immune-matching the donor to the recipient. This has important commercial advantages.

As used herein, "mesenchymoangioblast" or "MCA" refers to a cell that is a precursor to a MSC. A MSC may be produced by the method of the invention.

As used herein, "differentiating" refers to a process of a cell changing from one cell type to another, in particular a less specialized type of cell becoming a more specialized type of cell.

As used herein, "medium" or its plural "media" refers to a liquid or gel designed to support the growth of cells. In some embodiments, the cell culture medium comprises an IF9S medium. In some embodiments, the medium employs a 9S concentrated medium supplement, wherein dilution of the 9S concentrated medium supplement in an IMDM/F12 base medium yields an IF9S cell culture medium. The concentrated 9S medium supplement comprises 9 supplements as follows: L-ascorbic acid 2-phosphate Mg$^{2+}$ salt, 1-thioglycerol (monothioglycerol), additional sodium selenite, polyvinyl alcohol, GLUTAMAX™ (or glutamine), non-essential amino acids, chemically defined lipid concentrate, holo-transferrin, and insulin. In some embodiments, the concentrated 9S medium supplement comprises each component at a concentration 10× to 1000× of the final working concentration once diluted in a base medium. In one embodiment, an IF9S medium comprises IMDM, F12 and 9S as follows: IMDM 0.5×, F12 0.5×, sodium bicarbonate 2.1 mg/mL, L-ascorbic acid 2-phosphate Mg$^{2+}$ salt (64 µg/mL), 1-thioglycerol (50 µg/mL (460 µM, 40 µL/L)), sodium selenite (in addition to any present in the base medium; 8.4 ng/mL), polyvinyl alcohol (10 mg/mL), GLUTAMAX™ (1×), non-essential amino acids (1×), chemically defined lipid concentrate (1×), Holo-Transferrin (10.6 µg/mL), and insulin (20 µg/mL).

Although the presently disclosed media may include specific components (e.g. morphogens, small molecules, and hematopoietic cytokines), it is contemplated that other components with the same, equivalent, or similar properties may be used in addition to or in place of those disclosed, as are known in the art.

In some embodiments, components of an IF9S medium may be substituted. For example, ascorbic acid and 1-thioglycerol can be replaced with an optional supplement of a compound and/or a thiol-containing compound with antioxidant properties. GLUTAMAX™ can be replaced with an optional supplement of L-glutamine. "Non-essential amino acids", which is a general term for amino acids that the human body can produce from other amino acids, can be replaced with an optional supplement of amino acids. "Chemically defined lipid concentrate," which is a solution specifically distributed by Life Technologies, can be replaced with an optional supplement of lipids. Additional selenite, insulin, and holo-transferrin can be replaced with any insulin-transferrin-selenite supplement. Polyvinyl alcohol can be replaced with an optional supplement of a biologically inactive media thickening compound.

As used herein, "differentiation medium" refers to a medium designed to support the differentiation of cells, that is, supporting the process of a cell changing from one cell type to another. According to the method of the present invention, a differentiation medium is used to support the process of changing a human PSC into a $^{EMH}$lin$^-$KDR$^+$APLNR$^+$PDGFRalpha$^+$ primitive mesoderm cell with mesenchymoangioblast (MCA) potential.

In some embodiments, the concentration, in the differentiation medium, of: BMP4 is about 10 ng/mL to about 250 mg/mL; activin A is about 1 ng/mL to about 15 ng/mL; FGF2 is about 5 ng/mL to about 50 ng/mL; and LiCl is about 1 mM to about 2 mM.

In some embodiments, the concentration of BMP4 is in the differentiation medium is about 10 ng/mL, about 15 ng/mL, about 20 ng/mL, about 25 ng/mL, about 30 ng/mL, about 35 ng/mL, about 40 ng/mL, about 45 ng/mL, about 50 ng/mL, about 60 ng/mL, about 70 ng/mL, about 80 ng/mL, about 90 ng/mL, about 100 ng/mL, about 110 ng/mL, about 120 ng/mL, about 130 ng/mL, about 140 ng/mL, about 150 ng/mL, about 160 ng/mL, about 170 ng/mL, about 180 ng/mL, about 190 ng/mL, about 200 ng/mL, about 210 ng/mL, about 220 ng/mL, about 230 ng/mL, about 240 ng/mL, or about 250 ng/mL.

The concentration of activin A in the differentiation medium may be about 1 ng/mL, about 2 ng/mL, about 3 ng/mL, about 4 ng/mL, about 5 ng/mL, about 6 ng/mL, about 7 ng/mL, about 8 ng/mL, about 9 ng/mL, about 10 ng/mL, about 11 ng/mL, about 12 ng/mL, about 13 ng/mL, about 14 ng/mL, or about 15 ng/mL.

The concentration of FGF2 in the differentiation medium may be about 1 ng/mL, about 5 ng/mL, about 10 ng/mL, about 15 ng/mL, about 20 ng/mL, about 25 ng/mL, about 30 ng/mL, about 35 ng/mL, about 40 ng/mL, about 45 ng/mL, or about 50 ng/mL.

The concentration of LiCl in the differentiation medium may be about 0.5 mM, about 0.6 mM, about 0.7 mM, about 0.8 mM, about 0.9 mM, about 1 mM, about 1.1 mM, about 1.2 mM, about 1.3 mM, about 1.4 mM, about 1.5 mM, about 1.6 mM, about 1.7 mM, about 1.8 mM, about 1.9 mM, about 2 mM, about 2.1 mM, about 2.2 mM, about 2.3 mM, about 2.4 mM, or about 2.5 mM. Preferably, as understood in the art, concentration of LiCl in the differentiation medium may be about 2 mM.

In some embodiments, the differentiation medium comprises a base medium, L-ascorbic acid 2-phosphate $Mg^{2+}$ salt, 1-thioglycerol, sodium selenite (in addition to any present in the base medium), polyvinyl alcohol, GLUTAMAX™, non-essential amino acids, chemically defined lipid concentrate, holo-transferrin, and insulin. Suitable base media for the differentiation media described herein include, but are not limited to, Iscove's Modified Dulbecco's Medium/F12 (IMDM/F12), TeSR1 base medium (mTeSR1™ base medium, Stem Cell Technologies) without FGF2 and TGF-beta; DF4S base medium, which is Essential $8^{th}$ medium (Life Technologies; also known as "E8" medium) without FGF2 and TGF-beta, I4S base medium, which is DF4S base with Iscove's modified Dulbecco's medium (IMDM) instead of DMEM/F12, and IF4S base is DF4S base with IMDM/F12 instead of DMEM/F12. Preferably, the base medium to be used is albumin-free. IMDM/F12 is a highly enriched synthetic medium suited for rapidly proliferating, high-density cell cultures with an added nutrient mixture. These media are known to the person skilled in the art.

In some embodiments, the medium referred to herein as "IF9S", comprises IMDM/F12, L-ascorbic acid 2-phosphate $Mg^{2+}$ salt, 1-thioglycerol, sodium selenite (in addition to any present in the base medium), polyvinyl alcohol, GLUTAMAX™, non-essential amino acids, chemically defined lipid concentrate, Holo-Transferrin, and insulin.

As used herein, "mesenchymal colony forming medium (M-CFM)" refers to a medium designed to support the formation of mesenchymal colonies from $^{EMH}$lin$^-$KDR$^+$ APLNR$^+$PDGFRalpha$^+$ primitive mesoderm cells with mesenchymoangioblast (MCA) potential.

In some embodiments, the concentration, in the the M-CFM, of: LiCl is about 1 mM and FGF2 is about 10 ng/mL; or LiCl is about: 1 mM and FGF2 is about 20 ng/mL.

The concentration of FGF2 in the M-CFM may be about 1 ng/mL, about 5 ng/mL, about 10 ng/mL, about 15 ng/mL, about 20 ng/mL, about 25 ng/mL, about 30 ng/mL, about 35 ng/mL, about 40 ng/mL, about 45 ng/mL, or about 50 ng/mL.

The concentration of LiCl in the M-CFM may be about 0.5 mM, about 0.6 mM, about 0.7 mM, about 0.8 mM, about 0.9 mM, about 1 mM, about 1.1mM, about 1.2 mM, about 1.3 mM, about 1.4 mM, about 1.5 mM, about 1.6 mM, about 1.7 mM, about 1.8 mM, about 1.9 mM, about 2 mM, about 2.1 mM, about 2.2 mM, about 2.3 mM, about 2.4 mM, or about 2.5 mM. Preferably, the concentration of LiCl in the M-CFM is 1 mM. As noted above, inclusion of LiCl in a M-CFM to improve colony formation in clonogenic cultures was not known prior to the present invention and provides clear advantages for the method disclosed herein over methods known in the art.

As referred to herein, the term "defined medium" means that the identity and quantity of each component of a medium is known.

In some embodiments, media disclosed herein comprise xenogenic materials. As used herein, "xenogen" or "xenogenic" refers to non-human, biologically derived materials. Nonetheless, xenogenic materials may be defined. For example, a xenogenic material may be a recombinant protein of xenogenic origin. In one embodiment, the differentiation medium and/or the M-CFM comprises one or more xenogenic (e.g., recombinant non-human proteins).

In some embodiments, the medium is or the media are xenogen-free. Of central importance for clinical therapies is the absence of xenogenic materials in the derived cell populations, i.e., no non-human cells, cell fragments, sera, proteins, and the like. In one embodiment, xenogen-free differentiated cells are obtained using tenascin C or collagen IV, which essentially replaces contact with OP9 cells used in earlier differentiation systems.

Advantageously, defined media may be xenogen-free, and incorporate human proteins isolated from natural sources, such as from placenta or other human tissues, or that can be produced using recombinant technology. In some embodiments, all proteins described herein are human. In some embodiments, all of the proteins used in the differentiation medium are human proteins. In some embodiments all of the proteins used in the M-CFM medium are human proteins. In some embodiments, all proteins described herein are human recombinant proteins. In some embodiments, all of the proteins used in the differentiation medium are recombinant human proteins. In some embodiments all of the proteins used in the M-CFM medium are recombinant human proteins.

All proteins described herein are known to the person skilled in the art, and most if not all proteins described herein are available commercially.

Media disclosed herein may be also made in concentrated, including dried, forms that are diluted prior to use, such as 2×, 10×, 100×, or 1000× concentrations.

As used herein, "culturing" refers to the process by which cells are grown under controlled conditions.

Cells cannot be held in culture indefinitely owing to the increasing concentration of toxic metabolites, decreasing concentration of nutrients, and, for dividing cells, an increasing number of cells. As used herein, "passaging" refers to the process of producing a new culture with refreshed concentrations of nutrients, no toxic metabolites, and optionally a lower density of cells than the originating culture.

In one embodiment, passaging comprises: culturing the mesenchymal colony for about 3 days; culturing the mesenchymal colony on fibronectin and/or collagen I; and/or 1, 2, 3, 4, 5, or 6 passages. The number of passages may be 7, 8, 9, 10, 11, 12, 13, 14, 15, 16, 17, 18, 19, 20, 21, 22, 23, 24, or 25. Preferably the number of passages is 10 or fewer. More preferably, the number of passages is 5 or 6.

As used herein, "hypoxic" refers to conditions in which the oxygen concentration of the gas mixture is about 3% $O_2$ to about 10% $O_2$. In some embodiments, hypoxic conditions are about 5% $O_2$, but may be about 4% $O_2$, about 6% $O_2$, about 7% $O_2$, about 8% $O_2$, or about 9% $O_2$. In embodiments where a cell culture medium is allowed to equilibrate under hypoxic conditions, the cell culture medium becomes hypoxic owing to the lower concentration of oxygen dissolved in the medium compared to a cell culture medium equilibrated under normoxic conditions.

As used herein, "normoxic" refers to conditions in which the oxygen concentration of the gas mixture is about 20% $O_2$, but may be about 18% $O_2$, about 19% $O_2$, about 21% $O_2$, or about 22% $O_2$.

As used herein "AA" refers to activin A. In one embodiment, activin A exists as a homodimer of the polypeptide represented by the amino acid sequence provided in FIG. 1 as SEQ ID NO: 1.

As used herein, "BMP4" refers to bone morphogenic protein 4. In one embodiment, BMP4 exists as a homodimer of the polypeptide represented by the amino acid sequence provided in FIG. 2 as SEO ID NO: 2.

In one embodiment, "type I collagen" or "collagen I" exists as a triple helix trimer comprising two of the polypeptide represented by the amino acid sequence provided in FIG. 3 as SEQ ID NO: 3, and a third collagen I chain.

In one embodiment, "type IV collagen" or "collagen IV" exists as a triple helix heterotrimer comprising one of the polypeptide represented as the amino acid sequence provided in FIG. 4 as SEQ ID NO: 4, and two additional collagen IV chains.

As used herein, "FGF2" refers to fibroblast growth factor 2, also known as basic fibroblast growth factor. In one embodiment, FGF2 exists as a polypeptide represented as the amino acid sequence provided in FIG. 5 as SEQ ID NO: 5.

In one embodiment, fibronectin exists as a dimer of the polypeptide represented by the amino acid sequence provided in FIG. 6 as SEQ ID NO: 6.

As used herein, "PDGF" refers to platelet derived growth factor. In one embodiment, PDGF exists as a homodimer of the B subunit polypeptide represented by the amino acid sequence provided in FIG. 7 as SEQ ID NO: 7 (PDGF-BB). It is disclosed herein that supplementing M-CFM with PDGF (10 ng/mL) during culture had a significant negative impact on immune-suppression of iPSC-derived MSCs (4-fold reduction).

In one embodiment, "tenascin C" exists as a hexamer of the polypeptide represented by the amino acid sequence provided in FIG. 8 as SEQ ID NO: 8.

In some embodiments, adherent human PSCs are cultured on tenascin C or provided on a substrate treated with tenascin C. In some embodiments, any of the above-referenced cells (e.g., human PSCs, human iPSCs) are cultured on tenascin C. In some embodiments, any of the described cells are seeded on a substrate treated with an amount of tenascin C sufficient to adhere 10,000 cells/cm$^2$ to the substrate. In some embodiments, the tenascin C is human tenascin C (e.g. comprising an amino acid sequence represented by SEQ ID NO: 8. or provided by GenBank Accession No. CAA55309.1, or available commercially, e.g., Millipore Cat. No. CC065). In some embodiments, the substrate is treated with tenascin C at a concentration of at least about 0.25 µg/cm$^2$ to about 1 µg/cm$^2$, e.g., 0.3 µg/cm$^2$, 0.4 µg/cm$^2$, 0.5 µg/cm$^2$, 0.6 µg/cm$^2$, 0.7 µg/cm$^2$, 0.8 µg/cm$^2$, or 0.9 µg/cm$^2$. Cells can be grown on, e.g., tenascin C-coated cell culture dishes, multi-well cell culture plates, or microcarrier beads.

The use of tenascin C and hypoxic conditions may enable generation of $^{EMH}$lin$^-$KDR$^+$APLNR$^+$PDGFRalpha$^+$ primitive mesoderm cells with mesenchymoangioblast (MCA) potential and mesenchymal stem cells at higher percentages than compared to cells cultured on collagen IV or OP9 cells, such as greater than 10%, or greater than about 20%, or greater than about 30%, or greater than about 35%, or greater than about 40%, or greater than about 50%, or greater than about 60%, or greater than about 70%, or greater than about 80%, when compared per stage per platform.

As used herein, "superior T-cell immunosuppressive properties" refers to the capacity of a MSC to produce a greater magnitude of suppression of proliferation of T helper (CD4$^+$) lymphocytes, relative to a reference, for example as determined using an ImmunoPotency Assay.

Superior T-cell immunosuppressive properties may be about a 1% increase, about a 2% increase, about a 3% increase, about a 4% increase, about a 5% increase, about a 6% increase, about a 7% increase, about a 8% increase, about a 9% increase, about a 10% increase, about a 20% increase, about a 30% increase, about a 40% increase, about a 50% increase, about a 60% increase, about a 70% increase, about a 80% increase, about a 90% increase, about a 100%, or greater increase in T-cell immunosuppressive properties in an MSC or a population of MSC, produced according to the method disclosed herein. Alternatively, superior T-cell immunosuppressive properties may be about a 2-fold, about a 3-fold, about a 4-fold, about a 5-fold, about a 6-fold, about a 7-fold, about a 8-fold, about a 9-fold, about a 10-fold, or more increase in T-cell immunosuppressive properties in an MSC or a population of MSCs produced according to the method disclosed herein.

A suitable ImmunoPotency Assay uses an irradiated test MSC (e.g. iPSC-MSC produced according to the method disclosed herein) and an irradiated reference sample MSC, which are plated separately at various concentrations with carboxyfluorescein succinimidyl ester-labelled leukocytes purified from healthy donor peripheral blood. T helper (CD4+) lymphocytes that represent a subset of the reference sample are stimulated by adding CD3 and CD28 antibodies. CD4 labelled T cells are enumerated using flow cytometry to assess T cell proliferation. IC50 values are reported as a function of the reference sample. A higher IC50 value indicates a greater magnitude of suppression of proliferation of T helper (CD4$^+$) lymphocytes and thus is indicative of superior T-cell immunosuppressive properties. MSC samples are irradiated prior to use in this assay to eliminate the confounding factor of their proliferative potential.

It will be appreciated by the person skilled in the art that the exact manner of administering to a subject a therapeutically effective amount of an MSC or a population of MSCs differentiated according to the present method for treating a condition, disease or disorder will be at the discretion of the medical practitioner. The mode of administration, including dosage, combination with other agents, timing and frequency of administration, and the like, may be affected by the diagnosis of a subject's likely responsiveness to treatment with the MSC or population of MSCs, as well as the subject's condition and history.

As used herein, the term "therapeutic composition" refers to a composition comprising an MSC or population of MSCs as described herein that has been formulated for administration to a subject. Preferably, the therapeutic composition is sterile. In one embodiment, the therapeutic composition is pyrogen-free.

The MSC or population of MSCs will be formulated, dosed, and administered in a fashion consistent with good medical practice. Factors for consideration in this context include the particular type of disorder being treated, the particular subject being treated, the clinical condition of the subject, the site of administration, the method of administration, the scheduling of administration, possible side-effects and other factors known to medical practitioners. The therapeutically effective amount of the MSC or population of MSCs to be administered will be governed by such considerations.

The MSC or population of MSCs may be administered to a subject by any suitable method including intravenous (IV), intra-arterial, intramuscular, intraperitoneal, intracerobrospinal, subcutaneous (SC), intra-articular, intrasynovial, intrathecal, intracoronary, transendocardial, surgical implantation, topical and inhalation (e.g. intrapulmonary) routes. Most preferably, the MSC or population of MSCs is administered IV.

The term "therapeutically effective amount" refers to an amount of the MSC or population of MSCs effective to treat a condition, disease or disorder in a subject.

The terms "treat", "treating" or "treatment" refer to both therapeutic treatment and prophylactic or preventative measures, wherein the aim is to prevent or ameliorate a condition, disease or disorder in a subject or slow down (lessen) progression of a condition, disease or disorder in a subject. Subjects in need of treatment include those already with the condition, disease or disorder as well as those in which the condition, disease or disorder is to be prevented.

The terms "preventing", "prevention", "preventative" or "prophylactic" refers to keeping from occurring, or to hinder, defend from, or protect from the occurrence of a condition, a disease or disorder, including an abnormality or symptom. A subject in need of prevention may be prone to develop the condition, disease or disorder.

The term "ameliorate" or "amelioration" refers to a decrease, reduction or elimination of a condition, a disease or disorder, including an abnormality or symptom. A subject in need of treatment may already have the condition, disease or disorder, or may be prone to have the condition, disease or disorder, or may be in whom the condition, disease or disorder is to be prevented.

As used herein, the term "subject" refers to a mammal. The mammal may be a primate, particularly a human, or may be a domestic, zoo, or companion animal. Although it is particularly contemplated that the method and its resulting MSC or population of MSCs disclosed herein are suitable for medical treatment of humans, they are also applicable to veterinary treatment, including treatment of domestic animals such as horses, cattle and sheep, companion animals such as dogs and cats, or zoo animals such as felids, canids, bovids and ungulates.

EXAMPLES

Example 1

Reagents

TABLE 1

| Reagents | |
|---|---|
| Description | Vendor/Cat # or Ref # |
| DMEM/F12 Base Medium | Invitrogen/A1516901 |
| E8 supplement | Invitrogen/A1517101 |
| vitronectin | Life Technologies/A14700 |
| collagen IV | Sigma/C5533 |
| H-1152 ROCK Inhibitor | EMD Millipore/555550 |
| Y27632 dihydrochloride ROCK Inhibitor | Tocris/1254 |
| FGF2 | Waisman Biomanufacturing/WC-FGF2-FP |

TABLE 1-continued

| Reagents | |
|---|---|
| Description | Vendor/Cat # or Ref # |
| human endothelial-SFM | Life Technologies/11111-044 |
| stemline II hematopoietic stem cell expansion medium | Sigma/S0192 |
| GLUTAMAX | Invitrogen/35050-061 |
| insulin | Sigma/I9278 |
| lithium chloride (LiCl) | Sigma/L4408 |
| collagen I solution | Sigma/C2249 |
| fibronectin | Life Technologies/33016-015 |
| DMEM/F12 | Invitrogen/11330032 |
| recombinant human BMP4 | Peprotech/120-05ET |
| activin A | Peprotech/120-14E |
| Iscove's modified Dulbecco's medium (IMDM) | Invitrogen/12200036 |
| Ham's F12 nutrient mix | Invitrogen/21700075 |
| sodium bicarbonate | Sigma/S5761 |
| L-ascorbic acid 2-phosphate $Mg^{2+}$ | Sigma/A8960 |
| 1-thioglycerol | Sigma/M6145 |
| sodium selenite | Sigma/S5261 |
| non essential amino acids | HyClone/SH30853.01 |
| chemically defined lipid concentrate | Invitrogen/11905031 |
| embryo transfer grade water | Sigma/W1503 |
| polyvinyl alcohol (PVA) | MP Bio/151-941-83 |
| holo-transferrin | Sigma/T0665 |
| ES-CULT M3120 | Stem Cell Technologies/03120 |
| STEMSPAN serum-free expansion medium (SFEM) | Stem Cell Technologies/09650 |
| L-ascorbic acid | Sigma/A4544 |
| PDGF-BB | Peprotech/110-14B |

The reagents listed in Table 1 are known to the person skilled in the art and have accepted compositions, for example IMDM and Ham's F12. GLUTAMAX comprises L-alanyl-L-glutamine dipeptide, usually supplied at 200 mM in 0.85% NaCl. GLUTAMAX releases L-glutamine upon cleavage of the dipeptide bond by the cells being cultured. Chemically defined lipid concentrate comprises arachidonic acid 2 mg/L, cholesterol 220 mg/L, DL-alpha-tocopherol acetate 70 mg/L, linoleic acid 10 mg/L, linolenic acid 10 mg/L, myristic acid 10 mg/L, oleic acid 10 mg/L, palmitic acid 10 mg/L, palmitoleic acid 10 mg/L, pluronic F-68 90 g/L, stearic acid 10 mg/L, TWEEN 80® 2.2 g/L, and ethyl alcohol. H-1152 and Y27632 are highly potent, cell-permeable, selective ROCK (Rho-associated coiled coil forming protein serine/threonine kinase) inhibitors.

TABLE 2

| IF6S medium (10X concentration) | | |
|---|---|---|
| 10X IF6S | Quantity | Final Concentration |
| IMDM | 1 package, powder for 1 L | 5X |
| Ham's F12 nutrient mix | 1 package, powder for 1 L | 5X |
| sodium bicarbonate | 4.2 g | 21 mg/mL |
| L-ascorbic acid 2-phosphate $Mg^{2+}$ | 128 mg | 640 µg/mL |
| 1-thioglycerol | 80 µL | 4.6 mM |
| sodium selenite (0.7 mg/mL solution) | 24 µL | 84 ng/mL |
| GLUTAMAX | 20 mL | 10X |
| non essential amino acids | 20 mL | 10X |
| chemically defined lipid concentrate | 4 mL | 10X |
| embryo transfer grade water | To 200 mL | NA |

TABLE 3

IF9S medium (1X concentration; based on IF6S)

| IF9S | Quantity | Final Concentration |
|---|---|---|
| IF6S | 5 mL | 1X |
| polyvinyl alcohol (PVA; 20 mg/mL solution) | 25 mL | 10 mg/mL |
| holo-transferrin (10.6 mg/mL solution) | 50 μL | 10.6 μg/mL |
| insulin | 100 μL | 20 μg/mL |
| embryo transfer grade water | To 50 mL | NA |

TABLE 4

Differentiation medium (1X concentration; based on IF9S)

| Differentiation Medium | Quantity | Final Concentration |
|---|---|---|
| IF9S | 36 mL | 1X |
| FGF2 | 1.8 μg | 50 ng/mL |
| LiCl (2M solution) | 36 μL | 2 mM |
| BMP4 (100 μg/mL solution) | 18 μL | 50 ng/mL |
| Activin A (10 mg/mL solution) | 5.4 μL | 1.5 ng/mL |

TABLE 5

Mesenchymal colony forming medium (1X concentration)

| M-CFM | Quantity | Final Concentration |
|---|---|---|
| ES-CULT M3120 | 40 mL | 40% |
| STEMSPAN SFEM | 30 mL | 30% |
| human endothelial-SFM | 30 mL | 30% |
| GLUTAMAX | 1 mL | 1X |
| L-ascorbic acid (250 mM solution) | 100 μL | 250 μM |
| LiCl (2M solution) | 50 μL | 1 mM |
| 1-thioglycerol (100 mM solution) | 100 μL | 100 μM |
| FGF2 | 600 ng | 20 ng/mL |

TABLE 6

Mesenchymal serum-free expansion medium (1X concentration)

| M-SFEM | Quantity | Final Concentration |
|---|---|---|
| human endothelial-SFM | 5 L | 50% |
| STEMLINE II HSFM | 5 L | 50% |
| GLUTAMAX | 100 mL | 1X |
| 1-thioglycerol | 87 μL | 100 μM |
| FGF2 | 100 μg | 10 ng/mL |

Example 2

Protocol for Differentiating a Human PSC into a MSC

1. Thawed iPSCs in E8 Complete Medium (DMEM/F12 Base Medium+E8 Supplement)+1 μM H1152 on Vitronectin coated (0.5 μg/cm$^2$) plastic ware. Incubated plated iPSCs at 37° C., 5% $CO_2$, 20% $O_2$ (normoxic).

2. Expanded iPSCs three passages in E8 Complete Medium (without ROCK inhibitor) on Vitronectin coated (0.5 μg/cm$^2$) plastic ware and incubated at 37° C., 5% $CO_2$, 20% $O_2$ (normoxic) prior to initiating differentiation process.

3. Harvested and seeded iPSCs as single cells/small colonies at 5×10$^3$ cells/cm$^2$ on Collagen IV coated (0.5 μg/cm$^2$) plastic ware in E8 Complete Medium+10 μM Y27632 and incubated at 37° C., 5% $CO_2$, 20% $O_2$ (normoxic) for 24 h.

4. Replaced E8 Complete Medium+10 μM Y27632 with Differentiation Medium and incubated at 37° C., 5% $CO_2$, 5% $O_2$ (hypoxic) for 48 h.

5. Harvested colony forming cells from Differentiation Medium adherent culture as a single cell suspension, transferred to M-CFM suspension culture and incubated at 37° C., 5% $CO_2$, 20% $O_2$ (normoxic) for 12 days.

6. Harvested and seeded colonies (Passage 0) on Fibronectin/Collagen I coated (0.67 μg/cm$^2$ Fibronectin, 1.2 μg/cm$^2$ Collagen I) plastic ware in M-SFEM and incubated at 37° C., 5% $CO_2$, 20% $O_2$ (normoxic) for 3 days.

7. Harvested colonies and seeded as single cells (Passage 1) at 1.3×10$^4$ cells/cm$^2$ on Fibronectin/Collagen 1 coated plastic ware in M-SFEM and incubated at 37° C., 5% $CO_2$, 20% $O_2$ (normoxic) for 3 days.

8. Harvested and seeded as single cells (Passage 2) at 1.3×10$^4$ cells/cm$^2$ on Fibronectin/Collagen 1 coated plastic ware in M-SFEM and incubated at 37° C., 5% $CO_2$, 20% $O_2$ (normoxic) for 3 days.

9. Harvested and seeded as single cells (Passage 3) at 1.3×10$^4$ cells/cm$^2$ on Fibronectin/Collagen 1 coated plastic ware in M-SFEM and incubated at 37° C., 5% $CO_2$, 20% $O_2$ (normoxic) for 3 days.

10. Harvested and seeded as single cells (Passage 4) at 1.3×10$^4$ cells/cm$^2$ on Fibronectin/Collagen 1 coated plastic ware in M-SFEM and incubated at 37° C., 5% $CO_2$, 20% $O_2$ (normoxic) for 3 days.

11. Harvested and seeded as single cells (Passage 5) at 1.3×10$^4$ cells/cm$^2$ on Fibronectin/Collagen 1 coated plastic ware in M-SFEM and incubated at 37° C., 5% $CO_2$, 20% $O_2$ (normoxic) for 3 days.

12. Harvested as single cells and froze final product.

Two experiments (TC-A-96 and DAD-V-90) were executed to investigate the impact of supplementing M-CFM with PDGF-BB (10 ng/mL) and/or LiCl (1 mM) on T cell suppression of iPSC-MSCs. T cell suppression was evaluated generated using Waisman Biomanufacturing's ImmunoPotency Assay (IPA).

As outlined in Table 7, the following combinations of PDGF and LiCl were evaluated: PDGF+/LiCl+, PDGF−/LiCl−, PDGF+/LiCl− and PDGF−/LiCl+. Note that two different Dneg1 seed densities (5×10$^3$ cells/cm$^2$ and 1×10$^4$ cells/cm$^2$) and two different concentrations of activin A (AA) in the Differentiation Medium (1×AA=15 ng/mL and 0.1×AA=1.5 ng/mL) were compared in the TC-A-96 experiment. A single Dneg1 seed density (5×10e$^3$ cells/cm$^2$) and activin A concentration (1.5 ng/mL) were used in the DAD-V-90 experiment. Also note that a single leukopak (LPK7) was used in the first IPA (IPA 1) and two leukopaks (LPK7 and LPK8) were used in the second IPA (IPA 2).

This assay is designed to assess the degree to which each MSC line can suppress the proliferation of T helper (CD4+) lymphocytes. Cryopreserved MSCs are tested using cryopreserved leukocytes purified from the peripheral blood of healthy individuals (peripheral blood mononucleocyte cells (PBMC) derived from Leucopaks (LPK)). As such, LPK cell population variation is expected from donor to donor. Each MSC test sample is tested against the PMBC from two different individuals for clinical grade material with the option to limit testing to a single PMBC sample for research grade material. The assay for each MSC test sample is run in conjunction with a reference standard MSC line to ensure assay integrity/reproducibility and to normalize test samples. The assay is described in Bloom et al. *Cytotherapy*, 2015, 17(2):140-51.

In brief, test MSCs are exposed to 21 Gy of gamma irradiation. In a 48-well tissue culture plate $4\times10e^5$, $2\times10e^5$, $4\times10e^4$, and $2\times10e^4$ irradiated MSCs are plated into individual wells. PMBC are separately labelled with carboxyfluorescein succinimidyl ester. Labelled PMBC cells are plated at $4\times10^5$ cells per well containing the MSCs above. This results in titrated PBMC:MSC ratios of 1:1, 1:0.5, 1:0.1, and 1:0.05. An additional well is plated with stimulated PBMCs alone, another with MSCs alone, and another 1:0.05 ratio without stimulation, all which serve as controls. Subsequently, T cell-stimulatory monoclonal antibodies, anti-human CD3-epilson and anti-human CD28 (R&D Systems, Inc., Minneapolis, Minn.), are added to each well.

On day four of culture, cells are harvested from individual wells. Cells from each well are incubated with allophycocyanin-labelled anti-human CD4. CD4+ cells are then analysed for proliferation via carboxyfluorescein intensity using a flow cytometer. The MSC alone control serves to gate out MSCs from co-culture wells. The PBMC alone control serves as the positive control for maximum T cell proliferation against which the degree of MSC mediated suppression is measured. The non-stimulated 1:0.05 ratio well is used to generate a negative control gate against which proliferation is measured.

From test sample ratios a best fit curve is used to generate IC50 values. The IC50 values are normalized to the reference standard (IC50 Ref Std/IC50 Test Sample). This normalized IC50 yields larger values for more potent (more suppressive) samples and smaller values for less potent samples.

Results

IC50 data presented in Table 7 show that M-CFM supplemented with LiCl, but excluding PDGF (i.e. PDGF-/LiCl+) is optimal for differentiating of iPSCs to produce iPSC-MSCs that are immunosuppressive. Furthermore, a lower concentration of activin A also improved the immunosuppression of iPSC-MSCs.

3p, miR-299-5p. Each of the panel of 5 miRNAs was expressed in all of 71 MSC samples, but not 94 non-MSC samples, thereby enabling classification of cells as MSC or non-MSC.

The MSC produced according to Example 2 expressed each of miR-145-5p, miR-181b-5p, and miR-214-3p, but not miR-127-3p and miR-299-5p.

A principal component analysis of the 233 miRNAs of the microarray reliably detected in the normalised data (present in at least one sample tested) generated for all the samples tested demonstrated that the MSC produced according to Example 2 was distinct from each of the other 71 MSC samples (FIG. 9).

Example 4

Alternative Immunopotency Assay 1

Immunopotency of MSCs is evaluated as follows: human PBMCs from various donors are pooled (to minimise inter-individual variability in immune response) in phosphate-buffered saline and stained with carboxyfluorescein succinimidyl ester (CFSE, 2 μM) for 15 minutes at 37° C. in the dark, at a cell density of $2\times10^7$ PBMCs/mL. The reaction is stopped by adding an equal amount of RPMI-1640 medium supplemented with 10% human blood group AB serum. $3\times10^5$ CFSE labelled PBMCs resuspended in RPMI-1640 medium supplemented with 10% pooled human platelet lysate, 2 IU/mL preservative-free heparin (Biochrom), 2 mM L-glutamine, 10 mM (4-(2-hydroxyethyl)-1-piperazineethanesulfonic acid) (HEPES; Gibco), 100 IU/mL penicillin (Sigma) and 100 μg/mL streptomycin (Sigma) are then plated per well in triplicate in 96-well flat-bottomed plates (Corning). T-cell proliferation is determined using a Gallios 10-color flow cytometer and the Kaluza G1.0 software (both Coulter). Viable 7-aminoactinomycin-D-excluding (7-AAD-; BD Pharmingen) CD3-APC+ (eBioscience) T cells are analysed after 4 to 7 days. Proliferation kinetics and population distribution are analysed using Modfit 4.1 software (Verity).

TABLE 7

ImmunoPotency Assay

| IC50 (LPK7) | IC50 (LPK8) | Sample | PDGF | LiCl | Activin A | Seed Density (D2) |
|---|---|---|---|---|---|---|
| NA | not suppressive | TC-A-96-B3 | + | + | 0.1X (1.5 ng/mL) | $5 \times 10^3$ cells/cm$^2$ |
| NA | 0.17 | TC-A-96-B1 | + | + | 1X (15 ng/mL) | $5 \times 10^3$ cells/cm$^2$ |
| NA | 0.17 | DAD-V-90-4 | + | + | 0.1X (1.5 ng/mL) | $5 \times 10^3$ cells/cm$^2$ |
| NA | 0.19 | TC-A-96-D3 | + | + | 0.1X (1.5 ng/mL) | $1 \times 10^4$ cells/cm$^2$ |
| NA | 0.36 | DAD-V-90-2 | + | − | 0.1X (1.5 ng/mL) | $5 \times 10^3$ cells/cm$^2$ |
| NA | 0.57 | DAD-V-90-1 | − | − | 0.1X (1.5 ng/mL) | $5 \times 10^3$ cells/cm$^2$ |
| 0.39 | 0.54 | TC-A-96-B2 | − | + | 1X (15 ng/mL) | $5 \times 10^3$ cells/cm$^2$ |
| 0.37 | 0.58 | TC-A-96-D2 | − | + | 1X (15 ng/mL) | $1 \times 10^4$ cells/cm$^2$ |
| 0.69 | 0.93 | DAD-V-90-3 | − | + | 0.1X (1.5 ng/mL) | $5 \times 10^3$ cells/cm$^2$ |

NA—not applicable

Example 3

MSC MicroRNA Analysis

The MSC produced according to Example 2 underwent analysis against a microRNA (miRNA) microarray comprising 1194 miRNAs and a proprietary miRNA panel consisting of miR-127-3p, miR-145-5p, miR-181b-5p, miR-214-

Example 5

Alternative Immunopotency Assay 2

Immunopotency of MSCs is evaluated as follows: T helper (CD4+) lymphocytes are stained with CellTrace violet (CTV; Invitrogen) according to the manufacturer's instructions and then stimulated with anti-CD3/CD28- coated beads (Dynabeads, Invitrogen) at a T-cell/bead ratio of 5:1 in 96-well U-bottomed plates. Responder CD4 T cells are then incubated with irradiated (at 100 Gy) Karpas 299 cells (K299 cells; Sigma) as a reference standard, or MSCs. The co-cultured cells are incubated at 37° C. in 5% $CO_2$ in RPMI-1640 medium for 72 h. The cells are then washed with AnnexinV binding buffer (BD Biosciences) and stained with Annexin Vefluorescein isothiocyanate or APC (BD Biosciences) for 15 min in the dark at room temperature. After this incubation, the cells are stained with propidium iodide (PI) (Molecular Probes) and then immediately acquired on a LSRII Fortessa (BD Biosciences). Collected data are analysed with the use of FlowJo software (version 8.8.6; Tree Star). The viability is measured by the population of Annexin Venegative and PI-negative T cells. This proportion of viable cells is analysed for CTV dim (% proliferation). Suppression of T-cell proliferation is calculated by means of the equation: % Suppression=100−(a/b*100), where a is the percentage proliferation in the presence of suppressor cells and b is the percentage proliferation in the absence of suppressor cells.

Example 6

Treatment of Myocardial Infarction

Mesenchymal stem cells (MSCs) of the present disclosure were used in an experimental rat model of myocardial infarction (heart attack) to repair the rat heart after a heart attack.

Figure 10:
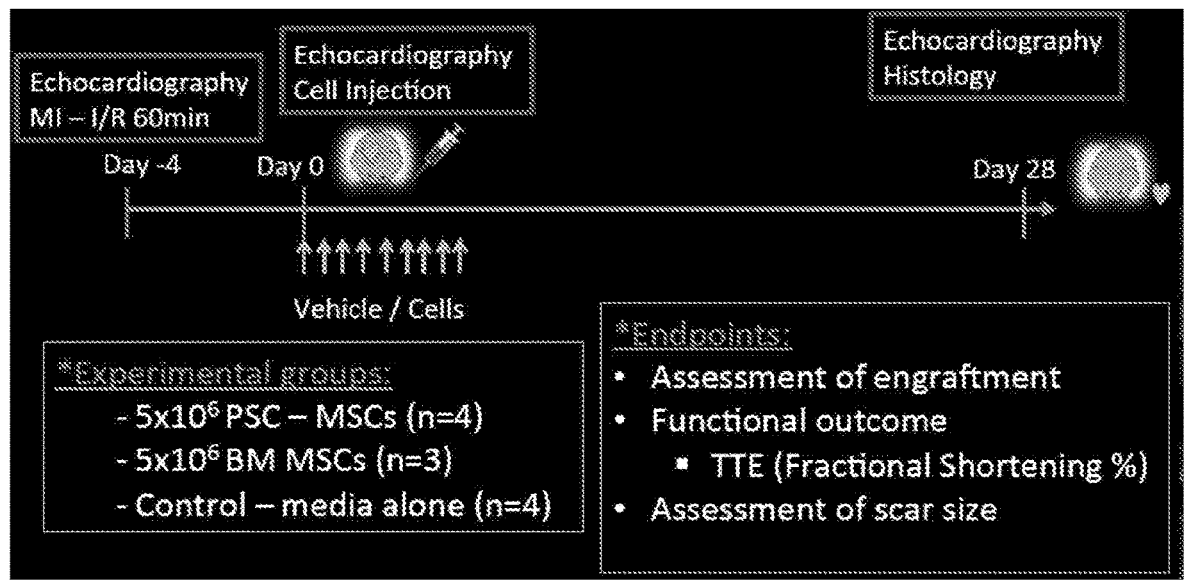
FIG. 10 is a schematic representation of the study of example 6.

Cardiac function and scar size were assessed over a 28 day period after a heart attack was induced in a total of 11 rats. Four animals were treated with the MSCs of the disclosure, three animals were treated with bone marrow-derived MSCs, and a further four animals received a placebo/vehicle control (FIG. 10).

Figure 11:
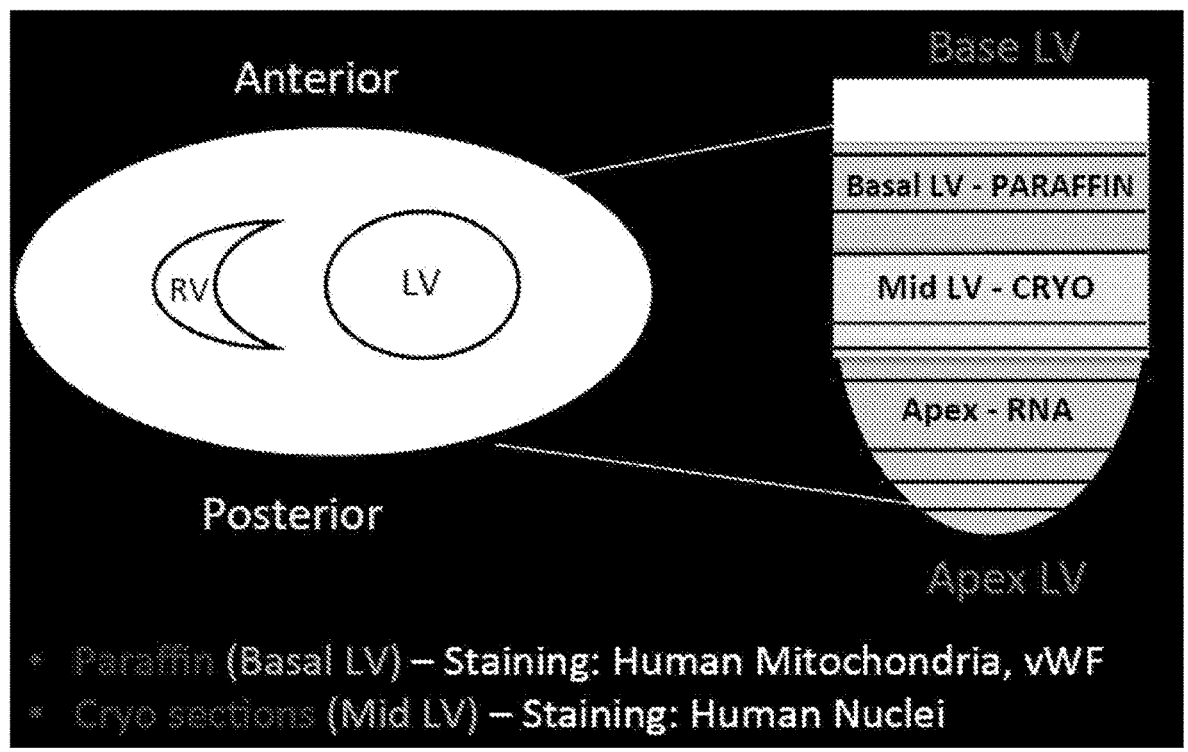
FIG. 11 is a schematic representation of the histology of the study of example 6.
Figure 12:
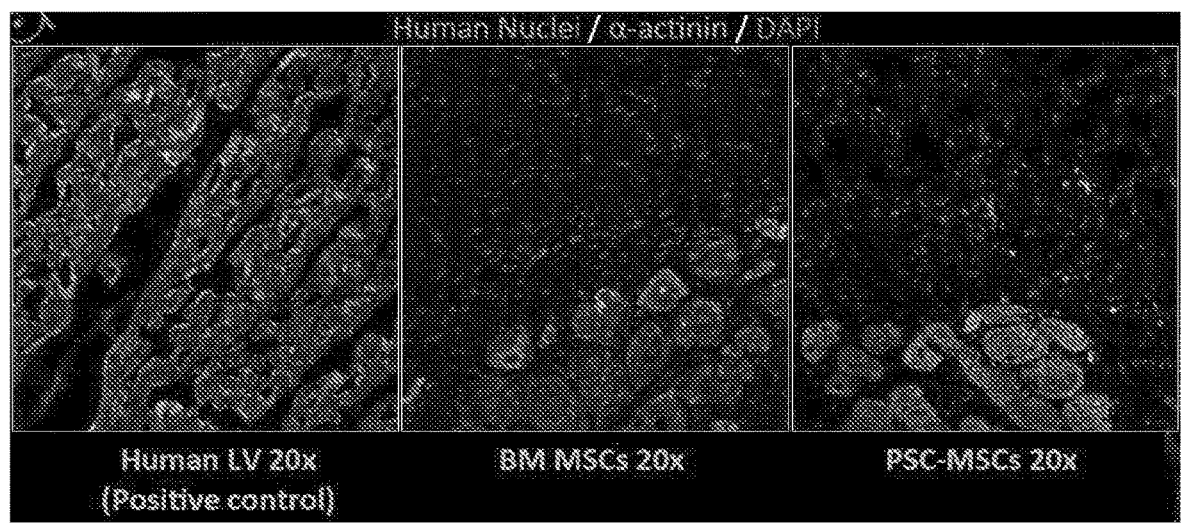
FIG. 12 comprises fluorescent photomicrographs of engraftment (human nuclei staining) of MSCs in the hearts of example 6. Human nuclei staining was performed at all levels in mid LV (cryo sections). There was no evidence of cell engraftment at day 28. Human mitochondria staining was performed at basal LV (paraffin sections). There was no evidence of cell engraftment at day 28.
Figure 13:
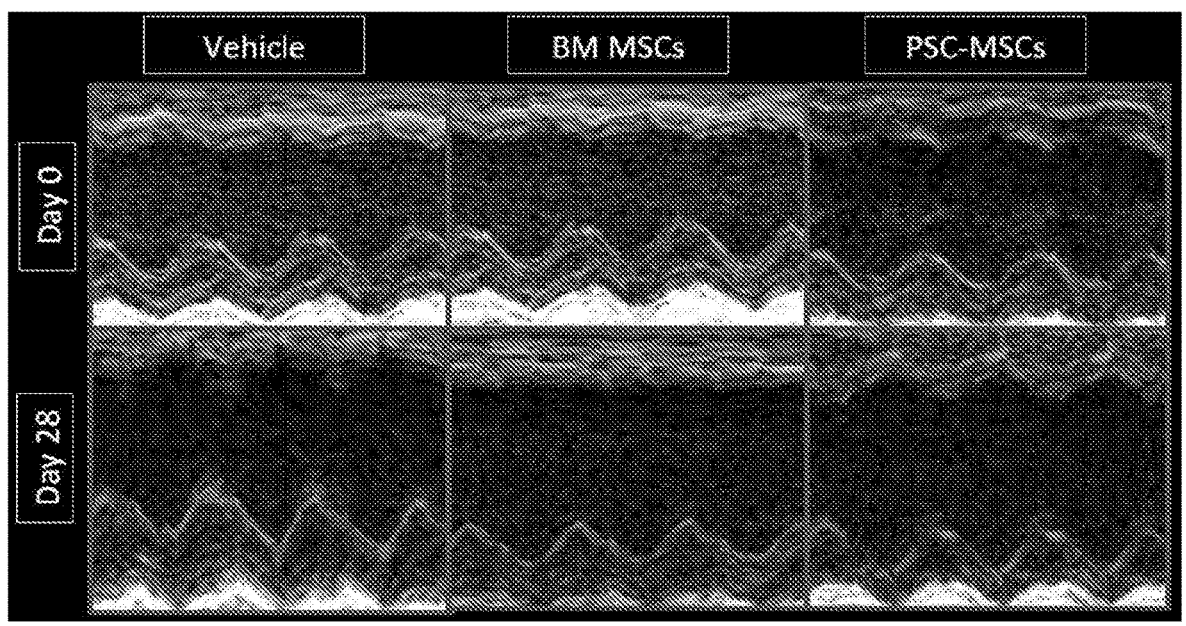
FIG. 13 shows functional assessment (TTE) and comprises short axis of M-mode images of hearts of vehicle, BM MSC, and PSC-MSC recipients of example 6 at baseline and 1 month time points. The images show reduced ventricular dilatation and increased ventricular contractility in the PSC-MSC recipients compared to the vehicle and BM MSC recipients.

Assessment of cell engraftment (FIGS. 11 and 12) showed:
 No evidence of cell engraftment using human nuclei and human mitochondria staining at day 28 in the BM-MSC and PSC-MSC groups Functional assessment (FIGS. 13 and 14) using fractional shortening (FS %) at day 28 compared to day 0 showed:
 minimal/no change in LV contractility in vehicle group
 LV contractility in BM MSC group
 LV contractility in PSC-MSC group Assessment of scar size (FIG. 15) showed:
 Apparent reduction in scar size on day 28 in PSC-MSC group (picosirius red) compared to vehicle and BM-MSCs group.

Figure 16:
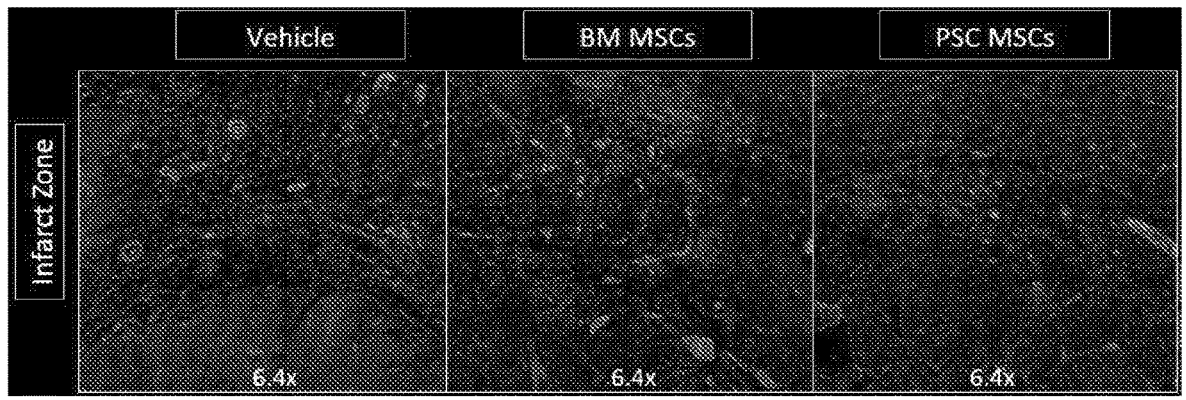
FIG. 16 comprises fluorescent photomicrographs assessing angiogenesis (vWF staining) in the hearts of example 6. The images show no difference in size and number of vessels between groups.

Assessment of angiogenesis (FIG. 16) showed:
 No obvious difference in size and number of vessels between groups (vWF staining).

The results showed that cardiac function was improved and scar size was reduced in the MSC recipients at day 28 compared to animals in both of the other groups. The results showed that the MSCs of the disclosure caused a substantial functional and structural improvement after a heart attack.

Figure 17:
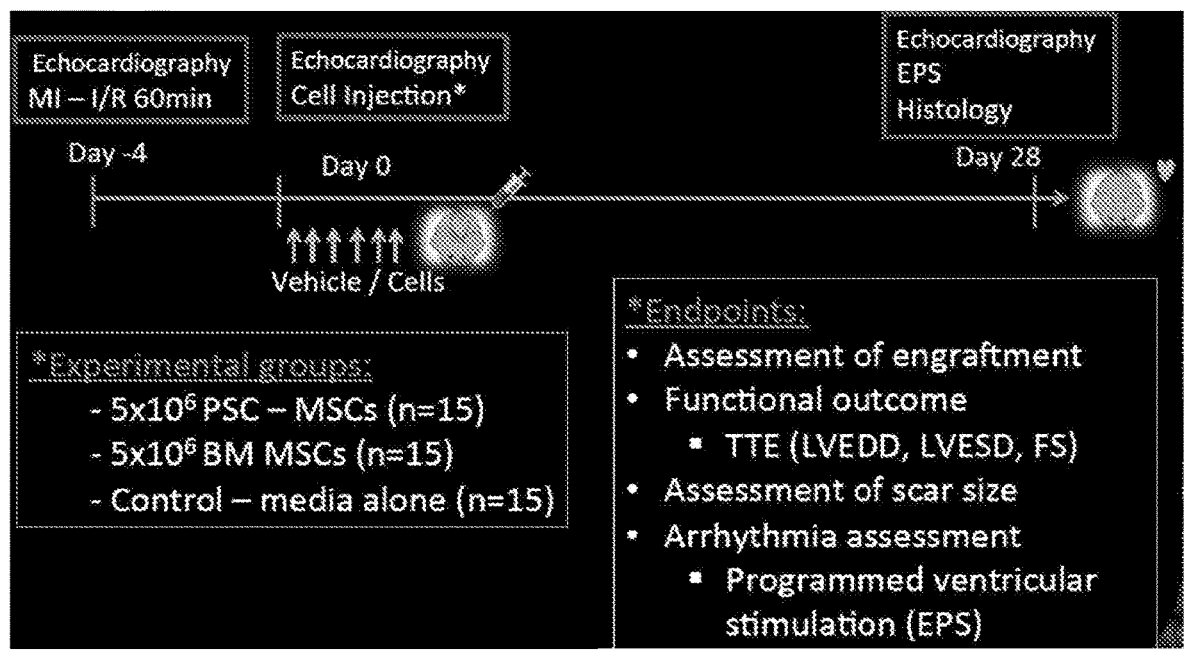
FIG. 17 is a schematic representation of a study similar to example 6.

In a modification of the study of example 6 as shown in FIG. 17, arrhythmia will be assessed using programmed ventricular stimulation (EPS).

Example 7

Treatment of GvHD

Animals were randomly assigned to treatment groups, and in all cases, the relevant treatment was injected via the tail vein. On day 0, six-week old female NOD.Cg-Prkdcscid Il2rgtm1Wjl/SzJ (NSG) mice were lightly irradiated with 2.5 Gy, then rested for 4 hours. GvHD was induced by intravenous (tail vein) transfer of 10 million human PBMCs. Following disease induction, mice were housed under pathogen-free conditions in micro-isolator cages and received acidified, antibiotic-supplemented water throughout the duration of the experimental procedures. The study design is summarised in Table 8.

TABLE 8

Summary of GvHD Study Design

| Group | Group description | PBMC Dose[1] | MSC Dose | n |
|---|---|---|---|---|
| Parts 1 and 2 - Survival studies | | | | |
| 1A | Irradiation controls (no GvHD) | 0 | 0 | 8 |
| 1B | GvHD controls[2] | $10 \times 10^6$ | 0 | 8 |
| 1C | Single dose controls (no GvHD) | 0 | $2 \times 10^6$ on d14 | 8 |
| 1D | MSC treated - single dose | $10 \times 10^6$ | $2 \times 10^6$ on d14 | 12 |
| 2A | Dual dose controls (no GvHD) | 0 | $2 \times 10^6$ on d14 & d18 | 8 |
| 2B | MSC treated - dual dose | $10 \times 10^6$ | $2 \times 10^6$ on d14 & d18 | 12 |

[1]All animals were lightly irradiated (2.5Gy) on Day 0. PBMCs were administered 4 hours after irradiation to induce GvHD (if applicable).
[2]GvHD controls received phosphate buffered saline (PBS) instead of MSC treatment.

Animals were assessed on a daily basis for GvHD signs/symptoms—i.e. weight loss, posture, activity, fur texture and skin integrity—as described in Table 9. An overall GvHD score was calculated by assigning 1 point for each Grade 1 sign/symptom and 2 points for each Grade 2 sign/symptom. Once a GvHD score of 8 or higher was reached in any animal, it was euthanised.

TABLE 9

GvHD grading

| Symptoms | Grade 0 | Grade 1 | Grade 2 |
|---|---|---|---|
| Weight loss | <10% | >10%; <20% | >20% |
| Posture | Normal | Hunching noted only at rest | Severe hunching and/or impairment of movement |
| Activity | Normal | Mild-moderate decrease | Stationary unless stimulated |
| Fur texture | Normal | Mild to moderate ruffling | Severe ruffling and poor grooming |

TABLE 9-continued

| GvHD grading | | | |
|---|---|---|---|
| Symptoms | Grade 0 | Grade 1 | Grade 2 |
| Skin integrity | Normal | Scaling of paws/tail | Obvious areas of denuded skin |

The primary endpoint was duration of survival.

Results iPSC-MSCs were thawed, washed, and resuspended in sterile PBS. Two million iPSC-MSCs were administered to relevant animals through the tail vein on day +14 (d14, single dose regimen) or on days +14 and +18 (d14, d18, dual-dose regimen).

The severity of GvHD was assessed using a standardised scoring system, which included five different criteria: weight loss, posture, activity, fur texture, and skin integrity. Mice were evaluated daily and scored from 0 (the least severe) to 2 (the most severe) for each criterion. Clinical scores were generated by adding scores for the five criteria. When a clinical score of "8" was reached, mice were removed from the study and humanely euthanised. The day of removal from the study was recorded as the day of lethal GvHD induction. Survival benefit was determined using Kaplan-Meier analysis with an applied log-rank test. p values of $\leq 0.05$ were considered significantly different.

Figure 18:
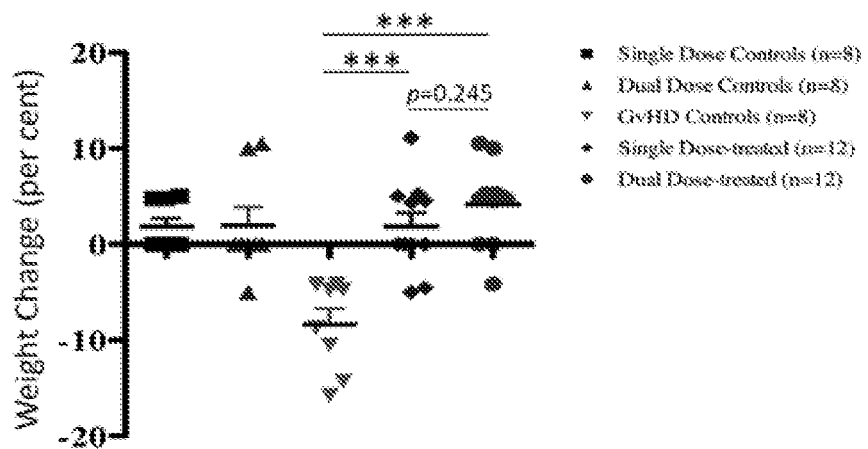
FIG. 18 is a scatter plot of percent weight change at day +19 of mice of example 7 relating to GvHD.

Animals receiving single- or dual-dose regimens of iPSC-MSCs showed significant relief from weight loss typically associated with this pre-clinical model (FIG. 18).

Figure 19:
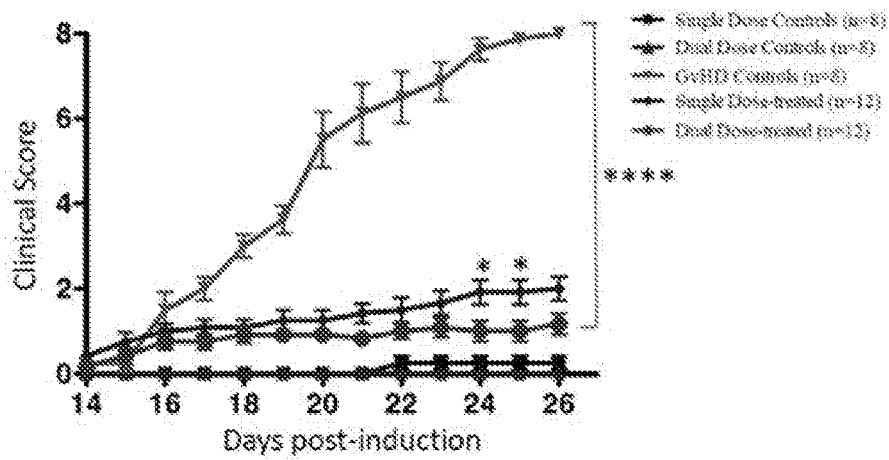
FIG. 19 is a line graph showing GvHD disease severity in mice of example 7.

Mice treated with single- or dual-dose regimens showed significant attenuation of disease symptoms, with further significant differences in symptoms noted between single- and dual-dose treatments on days +24 and +25 post-GvHD-induction (FIG. 19).

Figure 20:
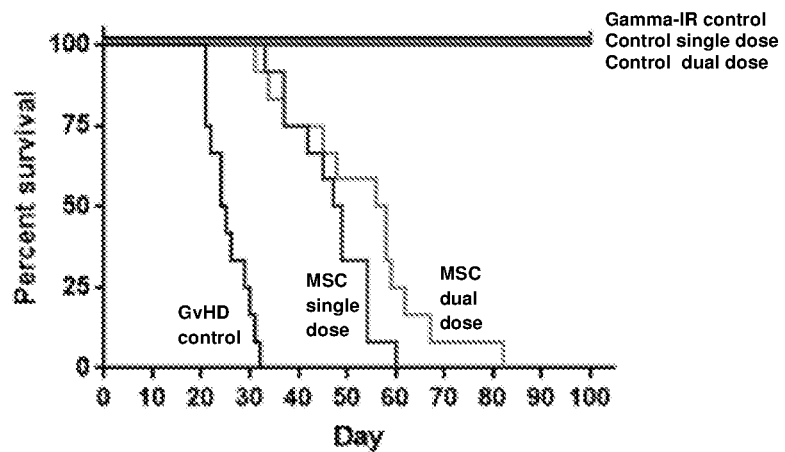
FIG. 20 is a Kaplan-Meier plot showing GvHD survival of mice of example 7.

In survival studies, single- and dual-dose treatments conferred significant survival benefits over GVHD controls ($p<0.0001$). Survival of animals receiving dual-dose regimens was slightly improved over single-dose-treated animals, although this increase did not reach statistical significance ($p=0.0715$). (FIG. 20)

From these survival studies, we conclude that CYMERUS™ iPSC-MSCs protect mice from weight loss, significantly attenuate disease severity, and provide a robust survival benefit when administered either in single- or dual-dose treatments, in a pre-clinical model of GvHD.

The invention claimed is:

1. A method for producing a mesenchymal stem cell (MSC), the method comprising:
   (a) culturing a primitive mesodermal cell in a mesenchymal-colony forming medium (M-CFM) comprising LiCl and FGF2, but excluding PDGF, BMP4 and Activin A, under normoxic conditions for sufficient time for a mesenchymal colony to form; and
   (b) culturing the mesenchymal colony of (a) adherently to produce the MSC,
   wherein the MSC of (b) has superior T-cell immunosuppressive properties relative to an MSC produced by a method comprising:
   (a') culturing a primitive mesodermal cell in a medium comprising FGF2 and PDGF, but excluding LiCl, under normoxic conditions for sufficient time for a mesenchymal colony to form; and
   (b') culturing the mesenchymal colony of (a') adherently to produce the MSC.

2. The method of claim 1, wherein the primitive mesodermal cell is a primitive mesodermal cell with mesenchymoangioblast (MCA) potential.

3. The method of claim 2, wherein the primitive mesodermal cell with MCA potential has a $^{EMH}$lin$^-$KDR$^+$APLNR$^+$PDGFRalpha$^+$ phenotype.

4. The method of claim 1, wherein sufficient time for the mesenchymal colony to form is about 8 days to about 14 days, about 10 days to about 14 days, about 11 to about 13 days, or about 12 days.

5. The method of claim 1, wherein the T-cell immunosuppressive properties of the MSC are determined relative to an MSC produced from a primitive mesodermal cell differentiated from a PSC in a differentiation medium comprising FGF2, BMP4, Activin A, and LiCl under hypoxic conditions for about two days.

6. The method of claim 1, wherein T-cell immunosuppressive properties comprise suppression of proliferation of T helper (CD4$^+$) lymphocytes.

7. The method of claim 1, wherein the M-CFM comprises about 1 mM LiCl.

8. The method of claim 1, wherein the M-CFM comprises about 5 ng/mL to about 100 ng/mL FGF2, about 10 ng/mL to about 50 ng/mL FGF2, about 10 ng/mL FGF2, or about 20 ng/mL FGF2.

9. The method of claim 1, wherein the M-CFM comprises about 1 mM LiCl and about 10 ng/mL FGF2, or about 1 mM LiCl and about 20 FGF2.

10. The method of claim 1, further comprising, prior to culturing the primitive mesodermal cell, differentiating a pluripotent stem cell (PSC) into a primitive mesodermal cell comprising:
    culturing; the PSC in a differentiation medium comprising FGF2, BMP4, Activin A, and LiCl under hypoxic conditions for about two days to form the primitive mesoderm; and
    replacing the differentiation medium with the M-CFM comprising LiCl and FGF2, but excluding PDGF.

11. The method of claim 1, wherein the cells are human.

12. The method of claim 10, wherein the PSC is an induced PSC (iPSC).

13. The method of claim 10, wherein the differentiation medium comprises:
    about 10 ng/mL to about 50 ng/mL FGF2, or about 50 ng/mL FGF2;
    about 50 ng/mL to about 250 ng/mL BMP4, or about 50 ng/mL BMP4;
    about 1 ng/mL to about 15 ng/mL Activin A, about 10 ng/mL to about 15 ng/mL Activin A, about 12.5 ng/mL Activin A, or about 1.5 ng/mL Activin A; and/or
    about 1 mM to about 2 mM LiCl.

14. The method of claim 10, wherein the differentiation medium comprises:
    about 50 ng/mL FGF2;
    about 50 ng/mL BMP4;
    about 1.5 ng/mL Activin A; and
    about 2 mM LiCl.

15. The method of claim 1, comprising culturing on collagen IV and/or tenascin C.

16. The method of claim 1, further comprising passaging the mesenchymal colony and/or MSC.

17. The method of claim 16, wherein passaging comprises:
    culturing the mesenchymal colony and/or MSC for about 3 days;
    culturing the mesenchymal colony and/or MSC on fibronectin and/or collagen I for 1, 2, 3, 4, 5, or 6 passages.

* * * * *